US008646344B2

(12) United States Patent
Israelachvili

(10) Patent No.: US 8,646,344 B2
(45) Date of Patent: Feb. 11, 2014

(54) MOUNTING SYSTEMS FOR A SURFACE FORCES APPARATUS

(71) Applicant: Jacob Israelachvili, Santa Barbara, CA (US)

(72) Inventor: Jacob Israelachvili, Santa Barbara, CA (US)

(*) Notice: Subject to any disclaimer, the term of this patent is extended or adjusted under 35 U.S.C. 154(b) by 6 days.

(21) Appl. No.: 13/681,898

(22) Filed: Nov. 20, 2012

(65) Prior Publication Data

US 2013/0327160 A1 Dec. 12, 2013

Related U.S. Application Data

(62) Division of application No. 13/493,954, filed on Jun. 11, 2012, now Pat. No. 8,371,182.

(51) Int. Cl.
*G01N 13/00* (2006.01)
*G01N 1/28* (2006.01)
*G01Q 30/20* (2010.01)

(52) U.S. Cl.
CPC .......... *G01N 13/00* (2013.01); *G01N 1/28* (2013.01); *G01Q 30/20* (2013.01)
USPC .......... 73/864.91; 73/866.5; 850/18

(58) Field of Classification Search
CPC .......... B01L 9/00; B01L 2200/02; B01L 2200/021–2200/022; B01L 2200/025; G01N 1/28; G01N 1/286; G01N 13/00; G01N 21/01; G01N 2021/0106; G01N 2201/021; G01Q 10/00; G01Q 10/02; G01Q 30/20

USPC .......... 73/1.08, 9–10, 53.05–53.06, 73/54.01–54.02, 54.22, 54.39, 64, 49, 73/64.55–64.56, 105, 841, 846, 73/862.041–862.043, 862.381, 862.541, 73/866.5; 250/428, 432, 576; 356/36, 72, 356/244, 440, 929; 422/561, 939, 422/FOR. 112; 850/1–2, 18, 53
See application file for complete search history.

(56) References Cited

U.S. PATENT DOCUMENTS

| 2,704,451 | A  | * | 3/1955 | Goeser .................... 73/846 X |
| 3,164,008 | A  | * | 1/1965 | Nielsen ..................... 356/32 |
| 5,315,860 | A  | * | 5/1994 | Dreilich et al. ............... 73/9 |
| 5,861,954 | A  | * | 1/1999 | Israelachvili ............. 356/496 |
| 6,752,001 | B1 | * | 6/2004 | LaPointe ..................... 73/10 |
| 8,016,218 | B1 | * | 9/2011 | Friedman ................. 241/175 |
| 8,189,199 | B2 | * | 5/2012 | Robertson et al. ......... 356/440 |
| 2013/0025380 | A1 | * | 1/2013 | Ross et al. ............... 73/864.91 |

FOREIGN PATENT DOCUMENTS

DE 3321237 A1 * 12/1984

* cited by examiner

*Primary Examiner* — Thomas P Noland
(74) *Attorney, Agent, or Firm* — Carr & Ferrell LLP

(57) ABSTRACT

A mounting system for samples and instruments for use with a measuring device such as a surface forces apparatus has a housing and a sample mount assembly positioned within the housing. The sample mount assembly has a pivot arm having a first edge and a flexing section. A spring has a first end coupled to the pivot arm. A first sample holder is coupled to the second end of the spring. A second sample holder is positioned in proximity to the first sample holder.

30 Claims, 21 Drawing Sheets

MOUNTING SYSTEMS FOR A SURFACE FORCES APPARATUS

RELATED APPLICATIONS

This application is a divisional and claims the priority benefit of co-pending U.S. patent application Ser. No. 13/493,954, filed Jun. 11, 2012, and entitled "Mounting Systems for a Surface Forces Apparatus," the disclosure of which is hereby incorporated by reference.

FIELD OF THE INVENTION

The present disclosure is directed generally to instrumentation for microscopic analysis, and more particularly to a sample mounting system for a surface forces apparatus that allows simultaneous measurement of a plurality of physical, chemical, biochemical, mechanical, or electrical properties.

BACKGROUND

Complex macromolecular and multimolecular systems may comprise nano-sized solute macromolecules such as proteins dispersed or dissolved in a liquid solvent, small liquid droplets or solid colloidal particles in a liquid, biological cells or membranes, and the like. An important physical property of these systems is the interaction potential between the particles or their surfaces in a suspending liquid medium or in a vapor atmosphere. The interaction potential is directly related to the interaction force between the particles or surfaces, both of which are usually formulated as functions of a separation distance, D, between the particles, or in the case of thin films, the two surfaces of film thickness, D.

The forces may be equilibrium forces (such as static or thermodynamic) or non-equilibrium forces (such as dynamic, transient, viscous, or rheological) that slowly change with time. The distances D may be measured directly, giving an absolute distance as in the surface forces apparatus (SFA) (see for example U.S. Pat. No. 5,861,954, the entire content of which is hereby incorporated by reference). Alternatively, the distance D may be measured indirectly, giving a relative or approximate distance as in the atomic force microscope (AFM).

Knowing these forces and their dynamics allows modeling of complex multicomponent systems where different molecules associate into various types of structures. These structures may then interact with each other through repulsive or attractive forces, leading to a stable dispersion of particles or an unstable dispersion where the particles slowly aggregate or coalesce and the system slowly changes or evolves over time. Biological or polymer systems composed of mixture of lipids, proteins, polyelectrolytes, and other complex molecules often have a very complex hierarchy of both their structures and their equilibration and relaxation times.

In almost every field of science, engineering, biology and medicine, there is a growing interest in understanding such systems. However, existing techniques may not be able to measure equilibrium and non-equilibrium forces in complex multimolecular and hierarchally structured systems because these techniques are often limited to measuring only one property. In addition, these techniques may be confined to measuring over a limited range of force, length, or time scales. In order to understand complex systems, it may be important to determine which molecules associate and which do not, as well as the structures that are formed by the associating molecules.

A better understanding of the structures formed by the association of complex molecules and their dynamics may be gained through the use of various types of direct or indirect visualization or imaging techniques simultaneously with measuring the equilibrium forces and/or non-equilibrium forces. These visualization and imaging techniques may include normal (optical) microscopy, fluorescence microscopy, fluorescence recovery after photobleaching (FRAP), confocal microscopy, reflective or grazing incidence x-ray scattering, and other techniques.

In addition to imaging the structures formed by the association of complex molecules, it may be beneficial to understand chemical reactions taking place between the molecules, particularly at the particle-solution interface. Such reactions may be studied by a variety of analytical techniques, such as IR-Raman spectroscopy, x-ray photoelectron spectroscopy (XPS), secondary ion mass spectrometry (SIMS), and energy-dispersive spectroscopy (EDS) in vacuum.

Structures may change over time as the forces within and between them change (with time). Many apparatus have been developed for directly measuring the forces between small particles or "probe tips" and surfaces (such as the AFM), and between two extended surfaces (such as the SFA). However, no single technique does both, nor allows simultaneous in situ ("real time") imaging capabilities.

SUMMARY

According to a first aspect of the present invention, there is provided a mounting system for a surface forces apparatus, the mounting system comprising: a housing comprising a plurality of sides defining a hollow space therein, at least one of the sides having an opening to provide access to the hollow space; a sample mount assembly comprising: a pivot arm comprising a first edge, a body portion and a flexing section extending between the first edge and the body portion; a spring having a first end and a second end, the first end being coupled to the body portion of the pivot arm; and a first sample holder coupled to the second end of the spring; and a second sample holder positioned in proximity to the first sample holder; the pivot arm being connected at said first edge to the housing to mount the sample mount assembly to the housing; whereby a force applied to the pivot arm causes the flexing section to bend and thereby move the body portion of the pivot arm relative to the first edge, thereby allowing adjustment of a distance between the first sample holder and the second sample holder.

According to a second aspect of the present invention, there is provided a mounting system for a surface forces apparatus, the mounting system comprising: a housing comprising a plurality of sides defining a hollow space therein; a pivot arm comprising a first edge, a body portion and a flexing section extending between the first edge and the body portion; a sample mount assembly mounted within the hollow space by the pivot arm, the sample mount assembly comprising a first sample holder; a second sample holder positioned in proximity to the first sample holder; and at least one load-applying device in contact with the pivot arm; the pivot arm being connected at the first edge to the housing to mount the sample mount assembly to the housing; whereby operation of the load-applying device causes the pivot arm to bend at the flexing section and thereby move the body portion of the pivot arm relative to the first edge, thereby allowing adjustment of a distance between the first sample holder and the second sample holder.

According to a third aspect of the present invention, there is provided a sample mount assembly for a surface forces apparatus, the sample mount assembly comprising: a pivot arm; the pivot arm comprising a flange along one edge for being received in a mounting slot of a surface forces apparatus; the pivot arm further comprising a body portion and a flexible section extending between the flange and the body portion such that the body portion can flex relative to the flange; the body portion having a mounting arrangement whereby a sample holder of the surface forces apparatus can be mounted to the body portion.

Embodiments of the present application may be used, for example, to measure interaction forces between at least two surfaces. Interaction forces may comprise adhesion, friction, viscous, and lubrication forces among others. Various embodiments may be used to perform measurements over a plurality of length and time scales.

Further features and advantages of the invention will become apparent from the following description of preferred embodiments of the invention, given by way of example only, which is made with reference to the accompanying drawings.

DETAILED DESCRIPTION

Examples of embodiments of the present invention relate to mounting systems for samples and instruments for use with a measuring device such as a surface forces apparatus. Various embodiments may comprise a housing or chamber made up of several sides defining a hollow space within the sides, at least one of the sides having an opening to provide access to the hollow space. A lower sample mount assembly may be positioned within the hollow space. The lower sample mount assembly may comprise a pivot arm with a flange along one edge and a flexing section extending from the flange. A spring having a first end and a second end may be coupled to the pivot arm at the first end, and a lower sample holder may be coupled to the second end of the spring. An upper sample holder may be positioned in proximity to the lower sample holder. In various embodiments, a force applied to the pivot arm may cause the flexing section to bend, thereby allowing adjustment of a distance between the lower sample holder and the upper sample holder.

Figure 1:
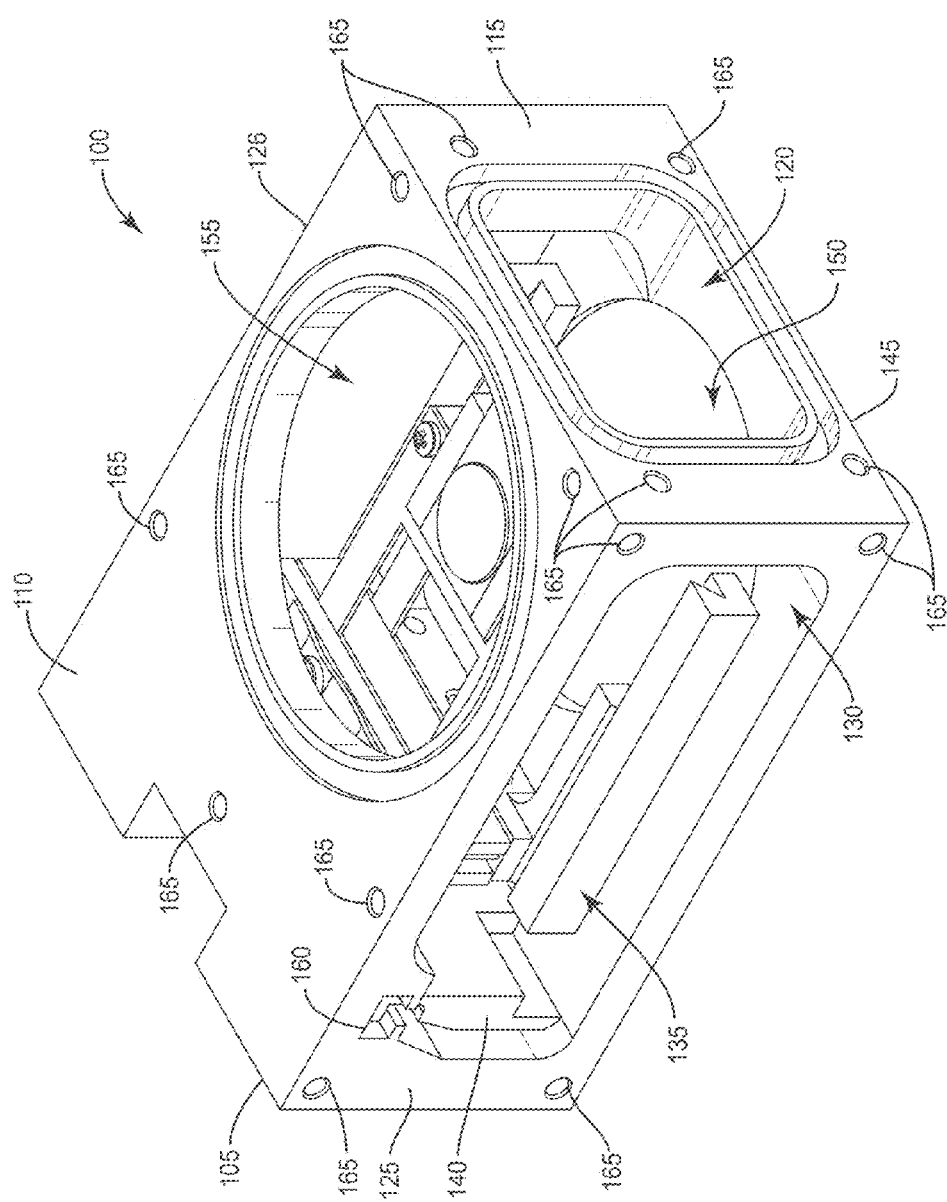
FIG. 1 is a perspective view of a housing and lower sample mount assembly.

FIG. 1 illustrates an example of a mounting system 100 for use with microscopic analysis devices, such as a surface forces apparatus (SFA), according to an embodiment of the present invention. The mounting system 100 comprises a chamber or housing 105 having a plurality of sides defining a hollow space therein, with a lower sample mount assembly 135 positioned within the hollow space. The housing 105 has a first side surface 125 with a large side opening 130 therethrough to allow access to the hollow space within the housing 105. Although not visible in FIG. 1, second side surface 126 directly opposite the first side surface 125 has an opening similar to the side opening 130 of the first side surface 125. In various embodiments, the side opening 130 is large enough for the lower sample mount assembly 135 to be inserted and removed through the side opening 130 without removing any other components attached to the housing 105, enabling easy access to and replacement of parts and attachments which are supported by the lower sample mount assembly 135 in use, as will be discussed further below. Pivot arm 140 of lower sample mount assembly 135 engages an elongate slot 160 which is provided laterally across the lower face of the upper surface 110 of the housing 105 and extends through side surface 125, allowing easy fitting and removal of the lower sample mount assembly 135 as discussed further below.

The housing 105 has a front surface 115 and front opening 120 within the front surface 115 to allow additional access to the hollow space within the housing 105. Front opening 120 provides access to the lower sample mount assembly 135 to facilitate rapid replacement or repositioning of a lower sample carried by the lower sample mount assembly 135. The housing 105 further has a bottom surface 145 which in this example has a window, wall opening 150, to allow for light or x-rays (or other electromagnetic waves) or a microscope objective to be directed into the housing 105 (see, for example, FIG. 11 discussed further below). The upper surface 110 has a top surface opening 155, which allows for insertion of an upper surface mount assembly (see, for example, FIG. 6 discussed further below).

Various embodiments may comprise one or more removable plates (see FIG. 22 and discussed further below) to cover the wall openings 120, 130, 150 and optionally seal the interior of the mounting system 100 while the mounting system 100 is in operation. Mounting holes 165 on side surface 125 and front surface 115 accept screws or bolts to secure the plates in place. Although not visible in FIG. 1, the side surface 126 and the bottom surface 145 also comprise mounting holes 165 which may be used in various embodiments to attach plates to cover the openings in those surfaces 126, 145. These and other features are described more fully below.

In various embodiments, the pivot arm 140 of the lower sample mount assembly 135 is adapted to accept a variety of different components or parts making up the upper mount assemblies (not shown in FIG. 1), lower sample mount assemblies 135, probes, sensors, actuators, gauges, and other attachments. This ability to accept many different upper and lower sample mounts and attachments, etc., allows the mounting system 100 to be used for one-dimensional, two-dimensional and three-dimensional force measurements with simultaneous imaging, such as optical interference "fringes of equal chromatic order" (FECO) or normal microscopic imaging, as well as a wide variety of other analyses within the same housing 105. Examples of such measurements and analyses which may be conducted include:

- One-, two-, and three-dimensional displacement measurement and simultaneous force measurement;
- Simultaneous fluorescence microscope imaging (including confocal and fluorescence recovery after photobleaching, FRAP) and chemical IR microscopy/spectroscopy;
- Simultaneous x-ray scattering/reflectivity and grazing incidence measurements;
- Simultaneous AFM-type scanning probe force measurements and profilometry (imaging);
- Ability to apply external electric fields across two interacting surfaces and the ability to detect internally generated electric fields, electric charging and currents between the two surfaces, as well as quantitatively study electrochemical reactions at and between two surfaces in aqueous solutions;
- Carry out tribological measurements (such as friction, lubrication, and thin film rheology) at low sliding speeds and high sliding speeds (up to about 20 meters/second, for example); and
- A variable speed friction and bio-sensing attachment for characterizing rheological and sensory properties of thin lubricating films and biological surfaces or fluids (such as blood rheology for early detection/diagnosis of blood disease), fluorescence imaging of micron-sized domains in biological membranes and tissues (such as for membrane-associated defects and diseases), food texture, and using live biosurfaces (such as quantitatively measuring the sensory perception of skin and hair).

Figure 2:
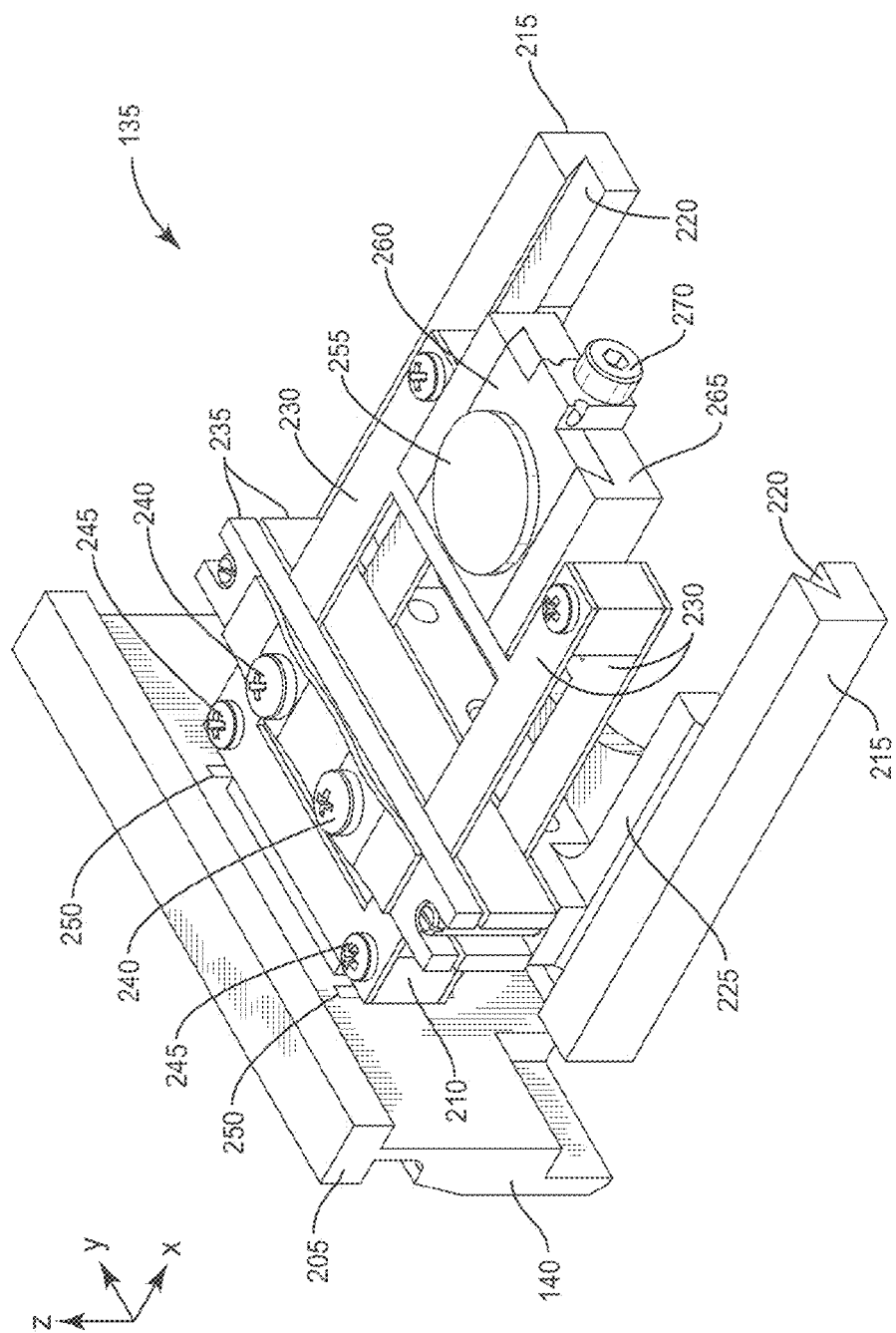
FIG. 2 is a perspective view of a lower sample mount assembly.

FIG. 2 illustrates in more detail an example of a lower sample mount assembly 135 which may be used for normal force measurements and simultaneous FECO, fluorescence, confocal, normal optical microscope or other imaging according to various embodiments. As described above and further below, the pivot arm 140 may be adapted to accept a variety of attachments that comprise the lower sample mount assembly 135.

The pivot arm 140 has an elongate flange 205 at its uppermost portion. The flange 205 is shaped to correspond to the slot 160 in the upper surface 110 of the housing 105 so that the flange 205 can be received in and retained by bolts in the slot 160 and therefore allow the pivot arm 140 to be rigidly mounted in the required position. The pivot arm 140 and indeed the lower sample mount assembly 135 as a whole can be passed through the side opening 130 in the first side surface 125, with the flange 205 engaging with the portion of the slot 160 that passes through the side surface 125, enabling the lower sample mount assembly 135 to be easily placed in position and removed from the housing 105 as required. As illustrated in FIG. 2, the flange 205 and slot 160 (FIG. 1) are rectangular in cross-section, although one skilled in the art will readily recognize that the flange 205 and slot 160 may take on other shapes such as round, triangular, trapezoidal, or any other polygon (simple or complex). In certain embodiments, the flange 205 and the slot 160 may each have a different shape.

The main generally rectangular body portion of the pivot arm 140 has two or more mounting slots 250 to accept fasteners such as screws or bolts (not shown) to secure a coupling block 210 to the pivot arm 140. The mounting slots 250 provide for movement of the coupling block 210 in the vertical or z-direction so that the coupling block 210 may be positioned initially approximately within the housing 105 as required. The coupling block 210 provides a mounting surface for guide rails or dove-tail sliders 215 and a first end of double cantilever springs 230 and thereby couples the guide rails 215 and the double cantilever springs 230 to the pivot arm 140 such that the guide rails 215 and the double cantilever springs 230 extend generally perpendicularly away (i.e., generally horizontally in use) from the main body portion of the pivot arm 140. Screws 245 are used to secure the first end of the cantilever springs 230 to the coupling block 210.

The guide rails 215 provide support and a movement guide for slider 225. V-shape grooves 220 along the length of the opposed inner faces of the guide rails 215 accept corresponding shape portions of the slider 225 to allow the slider 225 to slidably move in the x-direction towards and away from the pivot arm 140. A clamp assembly 235 is coupled to the slider 225 and moves in the x-direction as the slider 225 moves. The double cantilever springs 230 pass through the clamp assembly 235. By partially loosening or removing clamp screws 240 which pass into the clamp assembly 235, the clamp assembly 235 and slider 225 are freed to slide along the guide rails 215, and tightening of the clamp screws 240 clamps the clamp assembly 235 to the cantilever springs 230 to prevent movement of the clamp assembly 235 and slider 225. The stiffness of the double cantilever springs 230 can be adjusted by changing the position of the clamp assembly 235. Moving the clamp assembly 235 away from the pivot arm 140 shortens the effective length of the double cantilever springs 230 and increases the spring stiffness. Alternatively, moving the clamp assembly 235 closer to the pivot arm 140 increases the effective length of the double cantilever springs 230 and decreases the spring stiffness. In various embodiments, a ten-fold change in the free length of the springs 230 results in a thousandfold change in the spring stiffness, given that the spring stiffness of an end-clamped cantilever is inversely proportional to the cube of the free length of the cantilever. This adjustment of spring stiffness allows for forces ranging from very weak to very strong to be measured during the same experiment with the same basic apparatus and components. Moving the clamp assembly 235 as far as possible away from the pivot arm 140 may effectively eliminate spring movement and rigidly fix the double cantilever springs 230.

According to various embodiments, a lower sample disk mount holder 265 may be integrally formed with or coupled by screws or the like to the second end of the double cantilever springs 230 opposite the first end. The lower sample disk mount holder 265 has opposed V-shape grooves to slidably and releasably accept a lower sample disk mount 260 of dovetail cross-section, which in one embodiment supports or has a lower sample disk 255. A screw 270 secures the lower sample disk mount 260 to the lower sample disk mount holder 265. Referring back to FIG. 1, the lower sample disk mount 260 and the lower sample disk mount holder 265 may be accessible through the opening 120 in the front surface 115 of the housing 105. Thus, an operator may reach in through the opening 120, loosen the screw 270, and remove the lower sample disk mount 260 from the housing 105 through the opening 120. A new sample may then be placed on the lower sample disk 255 and then the lower sample disk mount 260 may be passed through the opening 120 and replaced in the lower sample disk mount holder 265, or a different lower sample disk 255 and lower sample disk mount 260 may be inserted.

Figure 3:
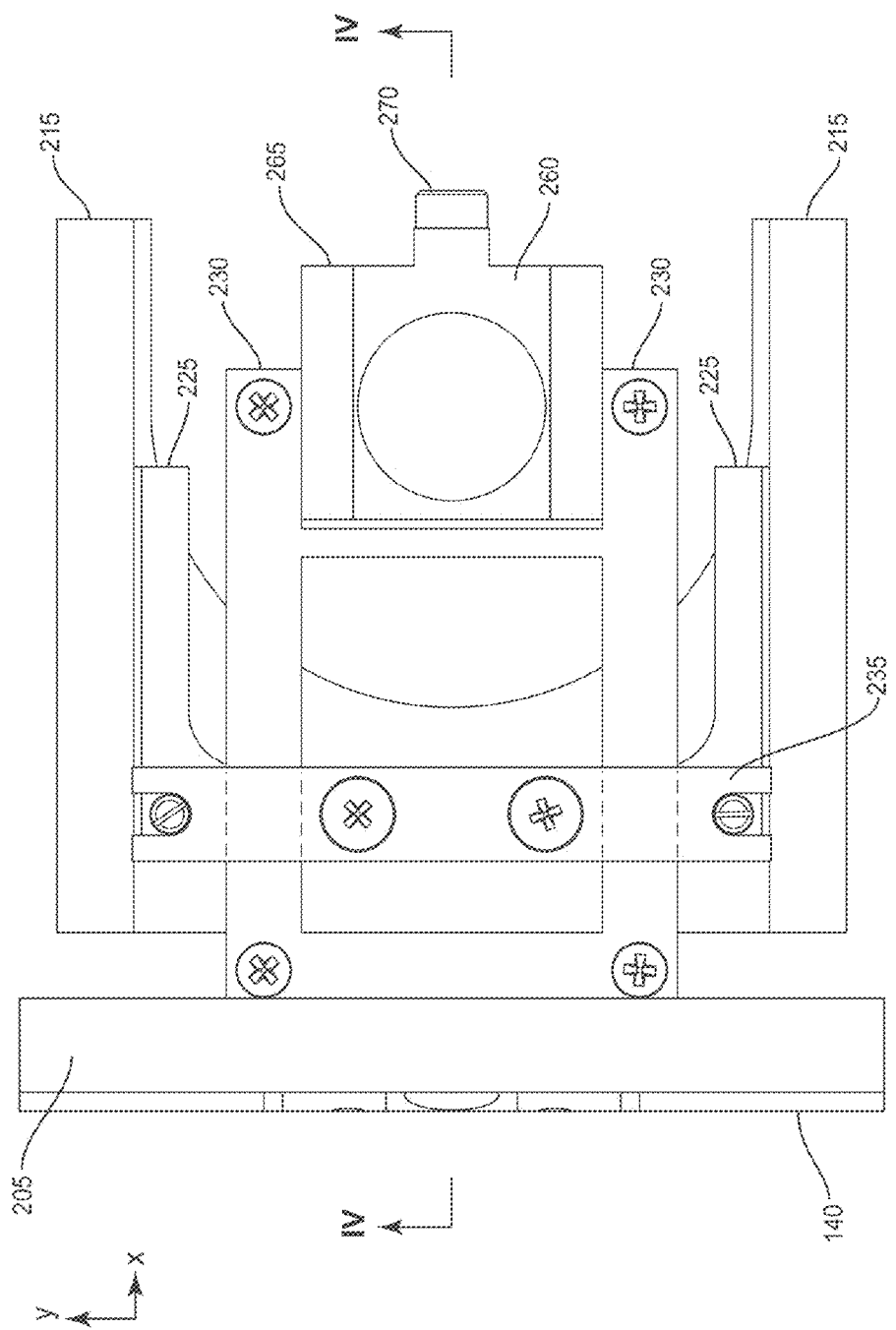
FIG. 3 is a top view of a lower sample mount assembly.

FIG. 3 illustrates a top view of the lower sample mount assembly 135 of FIG. 2. In this embodiment, the double cantilever springs 230 are coupled to either side of the lower sample disk mount holder 265, effectively eliminating movement of the lower sample disk mount holder 265 in the horizontal y-direction. As mentioned, the first end of each of the double cantilever springs 230 is coupled to the coupling block 210 (not visible in this view), which in turn is coupled to the pivot arm 140. This structure effectively eliminates movement of the lower sample disk mount holder 265 in the horizontal x-direction. Thus, movement of the lower sample disk mount holder 265 is allowed only in the vertical or z-direction (see FIG. 4).

Figure 4:
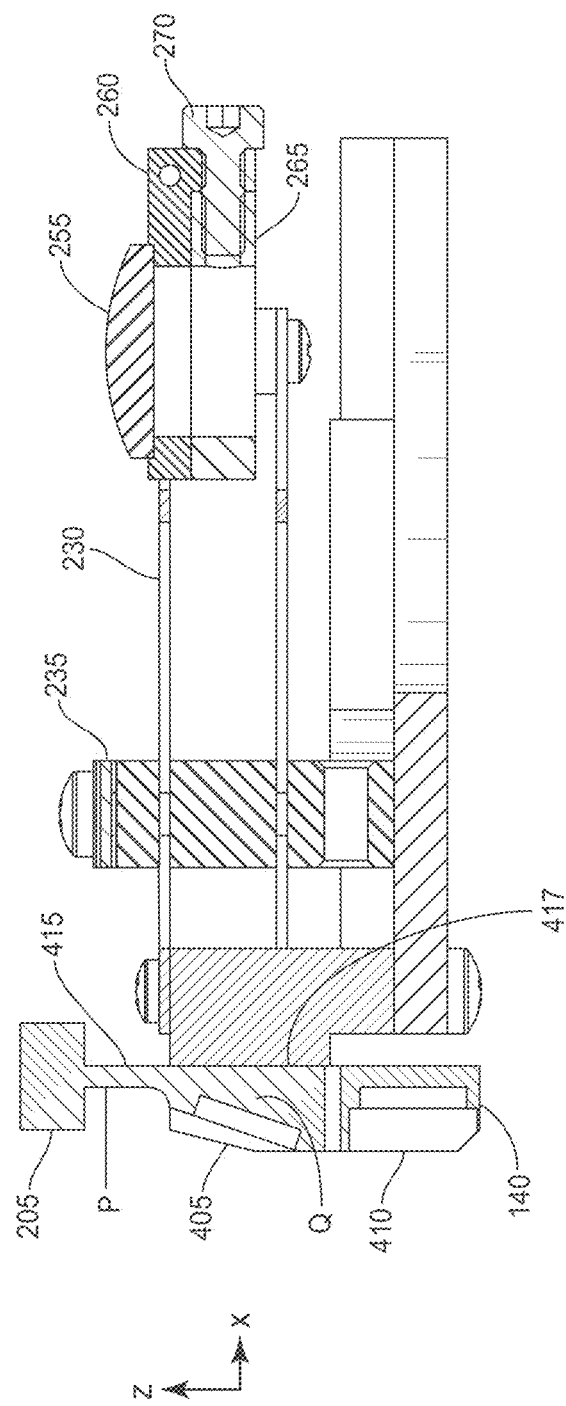
FIG. 4 is a cross-sectional view of a lower sample mount assembly.

FIG. 4 illustrates a cross-sectional side view of the lower sample mount assembly 135 in FIG. 3 according to various embodiments. There is shown the pivot arm 140 with the flange 205 extending along one (upper) edge and mounting section 417 in the main body portion which allows attachment of the lower sample mount assembly 135. The pivot arm 140 has a flexing section 415 between the flange 205 and the mounting section 417. The flexing section 415 extends from a lower side of the flange 205 to the main body portion of the pivot arm 140 and is thin enough to allow flexing generally in the region shown at P in the drawing when the flange 205 is securely engaged in the slot 160 and a force is applied to the pivot arm 140 below P. This force may be applied by a load-applying device, such as a linear actuator, a servo actuator, a screw, or any other electric, pneumatic, hydraulic, or manual device as is known per se. In various embodiments, the force may be applied by one or more micrometers, levers, or springs. A first micrometer M1 (not shown in FIG. 4, but visible in FIG. 10) may contact a sapphire or other suitably hard material disk 410 located on the pivot arm 140 and spaced apart from the flange 205 so as to be at the lower edge of the pivot arm 140 on the opposite side of P from the flange 205. Micrometer M1, which may be a differential micrometer in various embodiments, provides coarse distance control, for example, by pressing a ball-ended rotating shaft against the sapphire disk 410. This force causes the pivot arm 140 to flex generally at P. This flexing of the pivot arm 140 causes the main body portion of the pivot arm 140 to move in a generally arcuate motion around P. This causes a corresponding movement of the coupling block 210, which is fixed to the pivot arm 140, and therefore movement of the lower sample disk 255 which ultimately is supported by the coupling block 210 and therefore the pivot arm 140. Because P is located generally at the same horizontal (z-direction) level as the top of the lower sample disk 255, the movement in the x-direction of the lower sample disk 255 may be minimized and nearly all movement may be confined to the z-direction. In various embodiments, adjustment of the first micrometer M1 may move the lower sample disk 255 a total distance of about 4 mm (±2 mm about z=0) with a resolution of about 0.3-0.5 micron.

Figure 10:
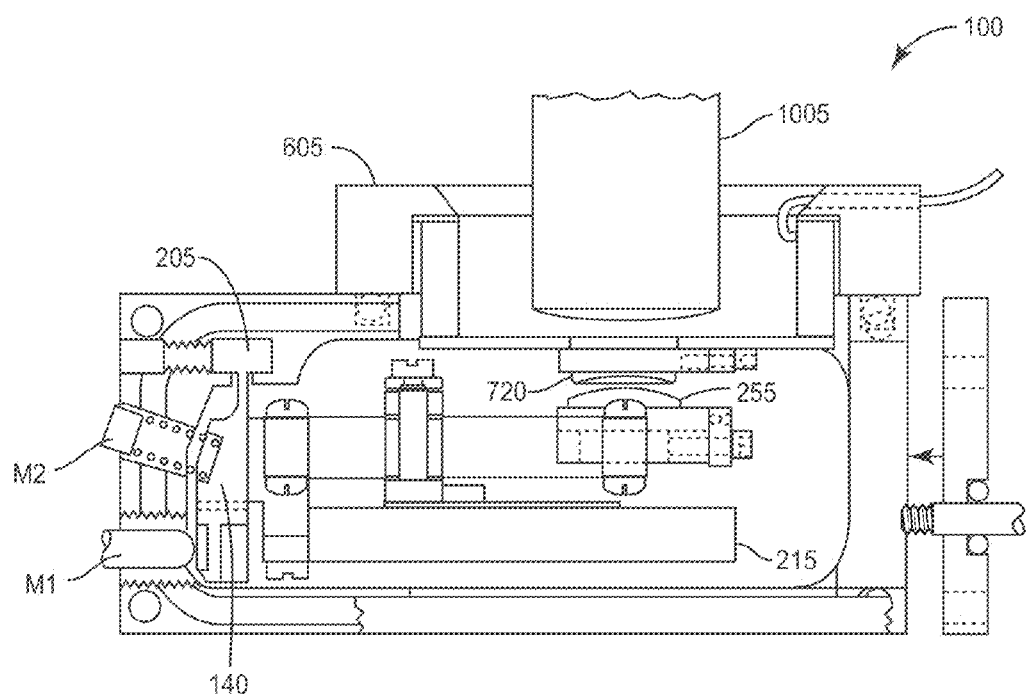
FIG. 10 is a cross-sectional view of a mounting system.

Fine distance control may be effected by a second micrometer M2 (not shown in FIG. 4, but visible in FIG. 10). This second micrometer M2 presses a helical coil spring against a spring seat 405 of the pivot arm 140 which is positioned below P but above the disk 410 against which the coarse micrometer M1 presses. In various embodiments, the second micrometer M2 may be a normal micrometer. The force acting at point Q may act also to rotate the pivot arm 140 about P, but by a much smaller distance compared to the movement caused by the first micrometer M1. In various embodiments, the movement distance may be determined by the ratio (of about 1000:1 in a particular example) of the stiffness of the flexing section 415 at P relative to that of the helical coil spring of the second micrometer M2, thereby allowing a motion of about 1 micron by the second micrometer M2 to be reduced to a movement of about 1 nm of the lower sample disk 255 in the z-direction. In various embodiments, one or more stiffness-adjustable antibacklash springs may press against the pivot arm 140, thereby minimizing or totally eliminating backlash and hysteresis.

As noted above, flexing of the pivot arm 140 at P results in motion of the lower sample disk 255 nearly exclusively in the z-direction. Movement in the x-direction may be very slight (e.g., sub nanometer) in various embodiments due to the circular motion of the lower sample disk 255 about point P. For example, a normal displacement of $\Delta z$ will produce a lateral shift $\Delta x$ in the x-direction given by the chord theorem of $\Delta x = \Delta z^2 / 2R$, where R is the distance between point P and the top of the lower sample disk 255 (the radius or locus of the circle). In a particular example, $R = 3.5$ cm $= 3.5 \times 10^{-2}$ m such that for $\Delta z = 100$ nm $= 10^{-7}$ m, which is about the maximum range of van der Waals or colloidal forces, the lateral shift $\Delta x$ is about $10^{-11}$ m $= 0.01$ nm, and even for $\Delta z = 1$ micron, $\Delta x$ is still negligible at about 1 nm.

This arrangement of the lower sample mount assembly 135, with the pivot arm 140 which supports the lower sample disk 255 and allows the lower sample disk 255 to be controllably moved vertically up and down, and which can be accessed through the side and front openings 130, 150 of the housing 105, provides a mounting system for a surface forces apparatus that is convenient and easy to use. Samples carried on the lower sample disk 255 can be easily changed or altered. The stiffness of the double cantilever springs 230 can be easily adjusted, allowing for adjustment of the amount of movement of the lower sample disk 255 achieved by application of force to one or both of the lower force disk 410 or upper spring seat 405. Furthermore, other devices, probes, attachments, etc., can be easily and conveniently fitted, as discussed in more detail below.

Figure 5:
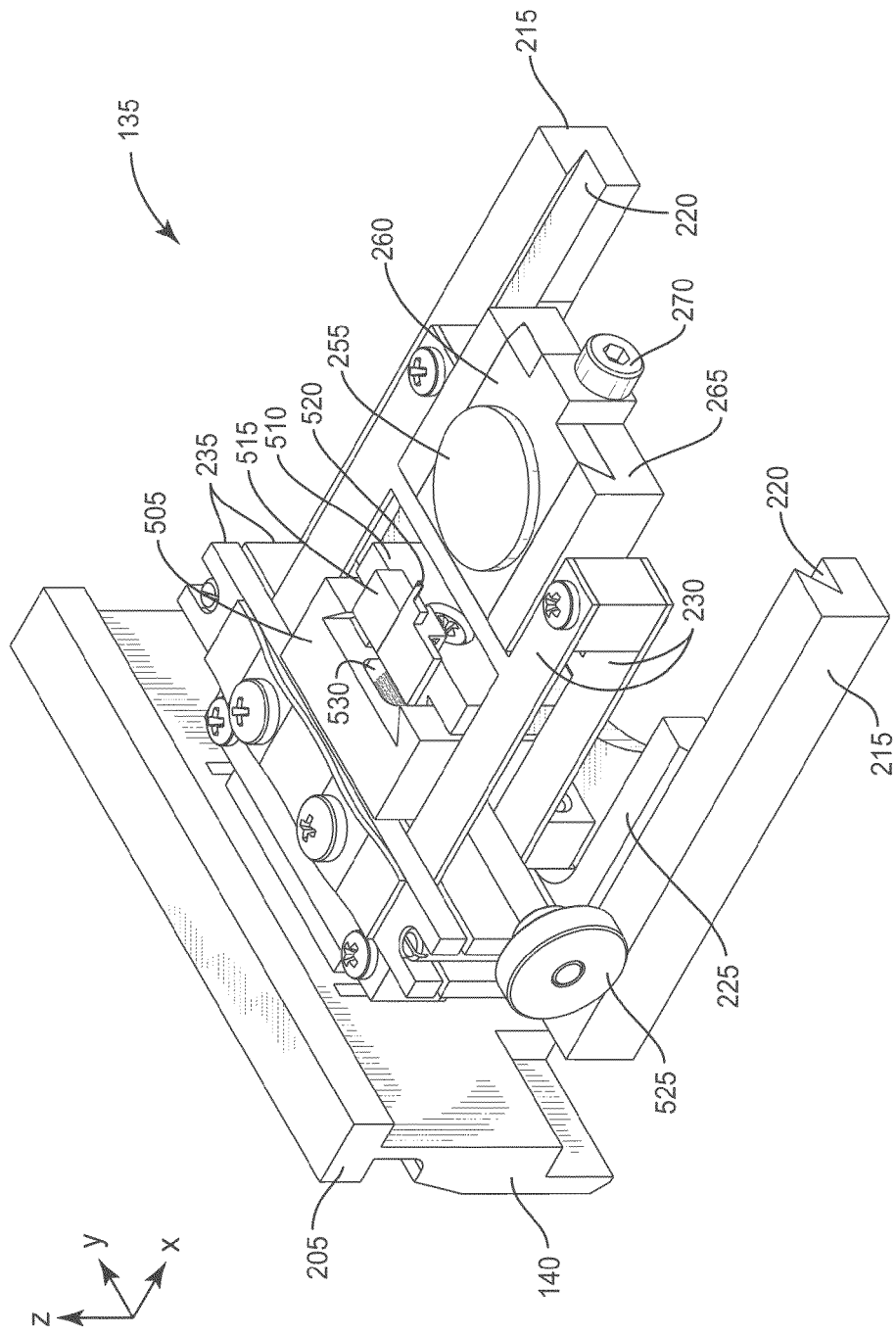
FIG. 5 is a perspective view of a lower sample mount assembly.

Various embodiments of the lower sample mount assembly 135 may be used in atomic force microscope (AFM) or scanning probe-type applications. AFM measurements may involve contacting a surface with a probe tip and measuring the displacement of the tip as the tip moves across the surface. FIG. 5 illustrates an embodiment of the lower sample mount assembly 135 that incorporates a probe tip 520. A probe tip mounting support 505 may be coupled to the slider 225 by one or more fasteners such as screws or bolts. A coarse probe tip height adjustment block 510 may be slidably engaged with the probe tip mounting support 505. An interchangeable probe tip assembly 515 with probe tip 520 extending outward may be coupled to the probe tip height adjustment block 510. A gear 530 may be mounted at least partially within the probe tip mounting support 505 such that teeth on the gear 530 engage a rack gear (not shown) on the probe tip height adjustment block 510. A probe tip height adjustment knob 525 may be operatively coupled to the gear 530 such that turning the adjustment knob 525 causes the gear 530 to rotate, thus moving the coarse probe tip height adjustment block 510 and the probe tip assembly 515 up and down in the z-direction. Although a rack and pinion gear is described here, one skilled in the art will recognize that any linear actuator is contemplated by the present disclosure.

As described above, the probe tip mounting support 505 may be coupled to the slider 225, such that the probe tip mounting support 505 follows the motion of the slider 225. In this "AFM-SFA" assembly, the cantilever spring screws 245 may be loosened or removed while the clamp screws 240 are tight, thereby allowing both the probe tip mounting support 505 and the lower sample disk mount holder 265 to move together when the slider 225 is moved across the guide rails 215. Thus, moving the slider 225 in the x-direction away from the pivot arm 140 may move the lower sample disk 255 away from an upper sample disk (an upper sample will be introduced in FIG. 7 below, and a dual AFM-SFA sample mounting system assembly will be introduced in FIGS. 15A and 15B), and allow the probe tip 520 to be positioned in proximity to an upper sample.

Figure 6:
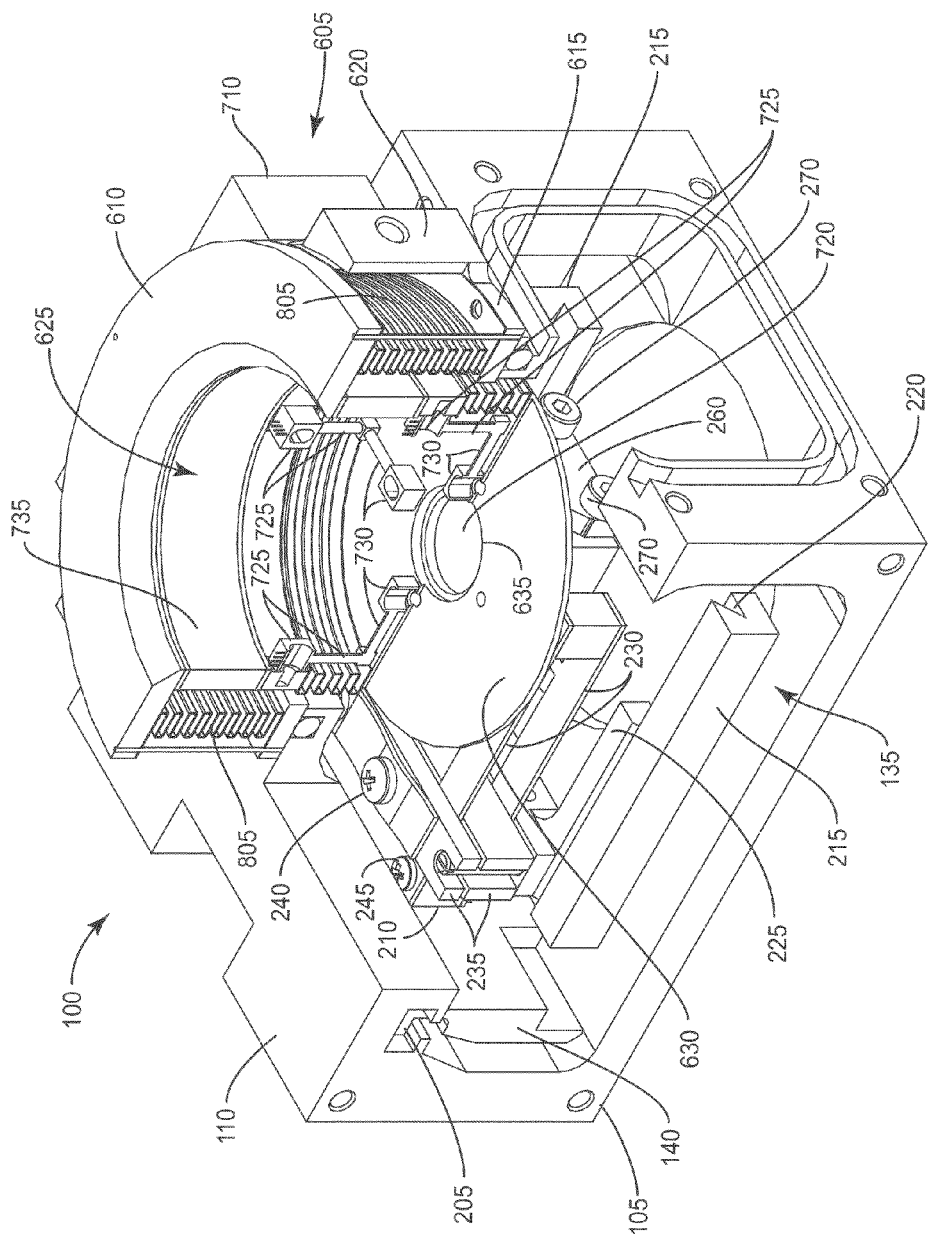
FIG. 6 is a perspective view of a mounting system.

In addition to a variety of lower sample mount assemblies, various embodiments of the present disclosure may also comprise upper sample mount assemblies to suit a particular experimental apparatus. For example, FIG. 6 illustrates a bellows upper mount assembly 605 having a bottom flange 615 that mates with the upper surface 110 of housing 105. In various embodiments, the bellows upper mount assembly 605 may comprise a hollow cylindrical center section 625 that aligns with the housing top surface opening 155 to provide access to the hollow space within the housing 105. The bellows upper mount assembly 605 may also comprise a top flange 610 to interface with other apparatus parts, such as first and second piezo-mechanical displacement actuators 710, 715 as shown in FIG. 7 that may be mounted to upper mount assembly accessory mounting blocks 620 as needed for a particular function.

Figures 7, 8:
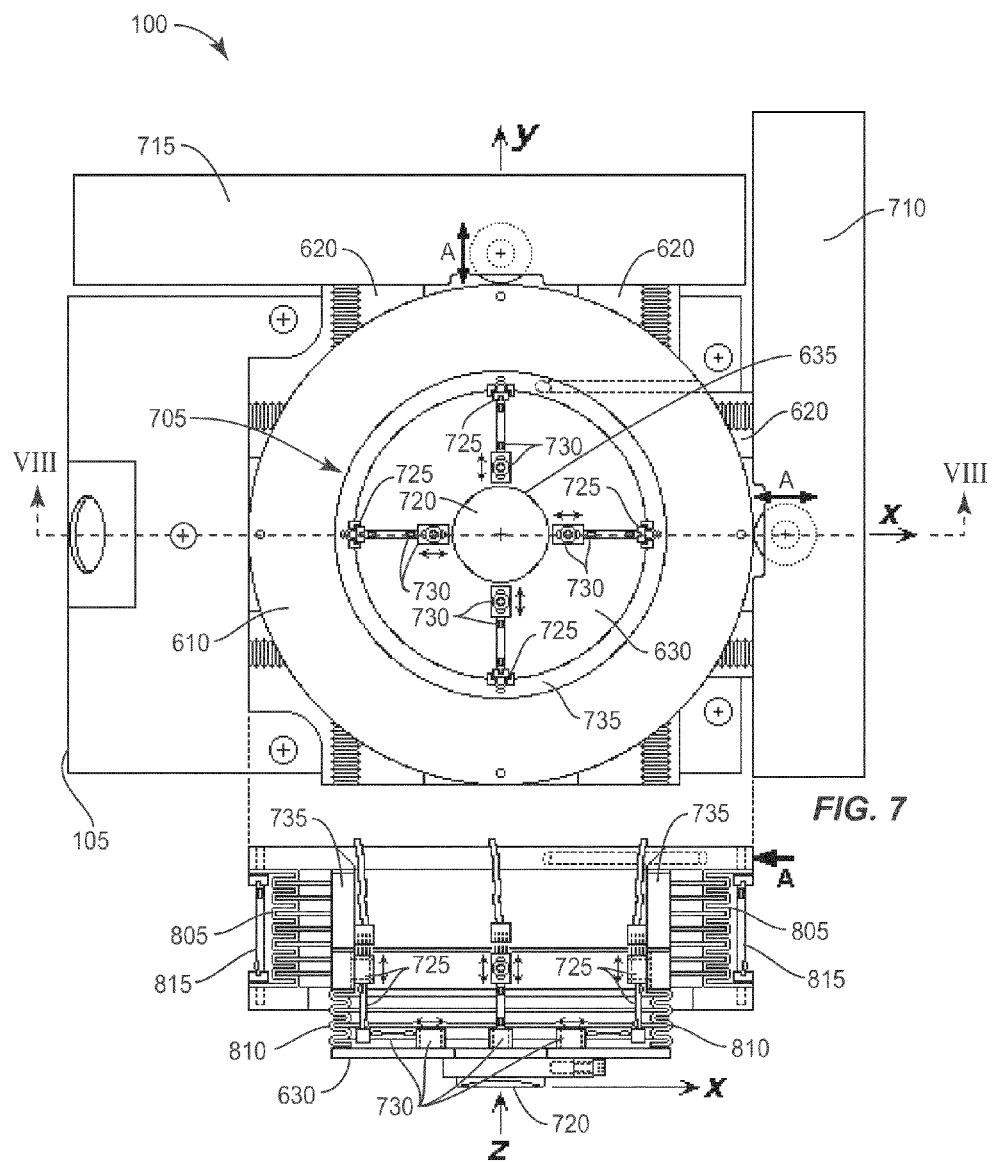
FIG. 7 is a top view of a mounting system.
FIG. 8 is a cross-sectional view of an upper sample mount assembly.

The bellows upper mount assembly 605 may comprise a bottom plate 630 to provide a mounting surface and support for vertical strain gauges 725 and horizontal strain gauges 730 (see also FIG. 7). The bottom plate 630 may have an opening 635 to facilitate mounting of a variety of probes and sample mounts. Additionally, the bottom plate 630 may help seal the bellows upper mount assembly 605 to prevent sensitive electronic devices located within the hollow cylindrical center section 625 from being exposed to damaging chemicals.

In various embodiments, the bellows upper mount assembly 605 may, for example, support a 3-dimensional actuator/sensor. FIGS. 7 and 8 illustrate a top view and side cross-sectional view, respectively, of the mounting system 100 with a 3-dimensional actuator/sensor upper sample mount assembly 705 coupled to the housing 105 by bellows upper mount assembly 605. The various embodiments illustrated in FIGS. 7 and 8 may provide independent 3-dimensional (x-direction, y-direction, and z-direction) motion of an upper sample disk 720 and simultaneous independent 3-dimensional sensing capabilities. First and second piezo-mechanical displacement actuators 710, 715 may be coupled to the upper mount assembly accessory mounting blocks 620 on two adjacent sides of upper mount assembly bottom flange 615 to provide independent motion in the x-direction and y-direction as indicated in FIG. 7. The piezo-mechanical displacement actuators 710, 715 may induce movement in either (or both) the x-direction or the y-direction at points A ranging from about 0.1 nm to about 2 mm.

According to various embodiments, a piezoelectric tube 735 may be coupled to the upper mount assembly upper flange 610 and extend at least partially into the hollow space within the bellows upper mount assembly 605, allowing for ultra-fine (0.1 nm to 10 μm) motion in the vertical z-direction. Coarse and fine vertical displacement in the z-direction may be effected by first micrometer M1 and second micrometer M2 as described previously. Lateral displacement (in the x-y plane) of the upper flange 610 relative to the bottom flange 615 (which may be fixed to the housing 105) may be measured by a plurality of flange strain gauges 815. The strain gauges 815 may, for example, be piezo-resistive, semi-conducting, or foil strain gauges and may comprise one or more Wheatstone bridge networks. As illustrated in FIG. 8, the upper flange 610 may be coupled to outer bellows 805. According to various embodiments, the outer bellows 805 may be fabricated from a compliant material that flexes to allow movement of the upper flange 610 in the x-y plane.

Normal forces (such as repulsive colloidal or attractive adhesion forces) acting on the upper sample disk 720 due to interaction with the lower sample disk 255 may be measured by a plurality of horizontal wires coupled to horizontal strain gauges 730 that may in turn be coupled to the upper mount assembly bottom flange 615 in an array about the upper sample disk 720. The horizontal strain gauges 730 may, for example, be piezo-resistive, semi-conducting, or foil strain gauges. The horizontal strain gauges 730 may comprise one or more Wheatstone bridge networks. Normal forces may also be measured by attaching strain gauges 730 to the double cantilever springs 230. Lateral forces (such as frictional or shear forces) acting on the upper sample disk 720 when sliding (or sticking) in the x-direction and/or y-direction relative to the lower sample disk 255 (which may be held in a fixed position) may be measured by a plurality of vertical wires coupled to vertical strain gauges 725 arrayed about the piezoelectric tube 735. The vertical strain gauges 725 may, for example, be piezo-resistive, semi-conducting, or foil strain gauges. The vertical strain gauges 725 may comprise one or more Wheatstone bridge networks.

In various embodiments, the outer bellows 805 and the inner bellows 810 may hermetically seal the 3-dimensional upper sample mount 705, effectively isolating the strain gauges 725, 730 from any potentially corrosive liquid or vapors inside the housing 105. This arrangement allows the use of delicate miniaturized electronic instruments, wires, and connectors while exposing the lower and upper sample disks 255, 720 to extreme environments.

Figure 9:
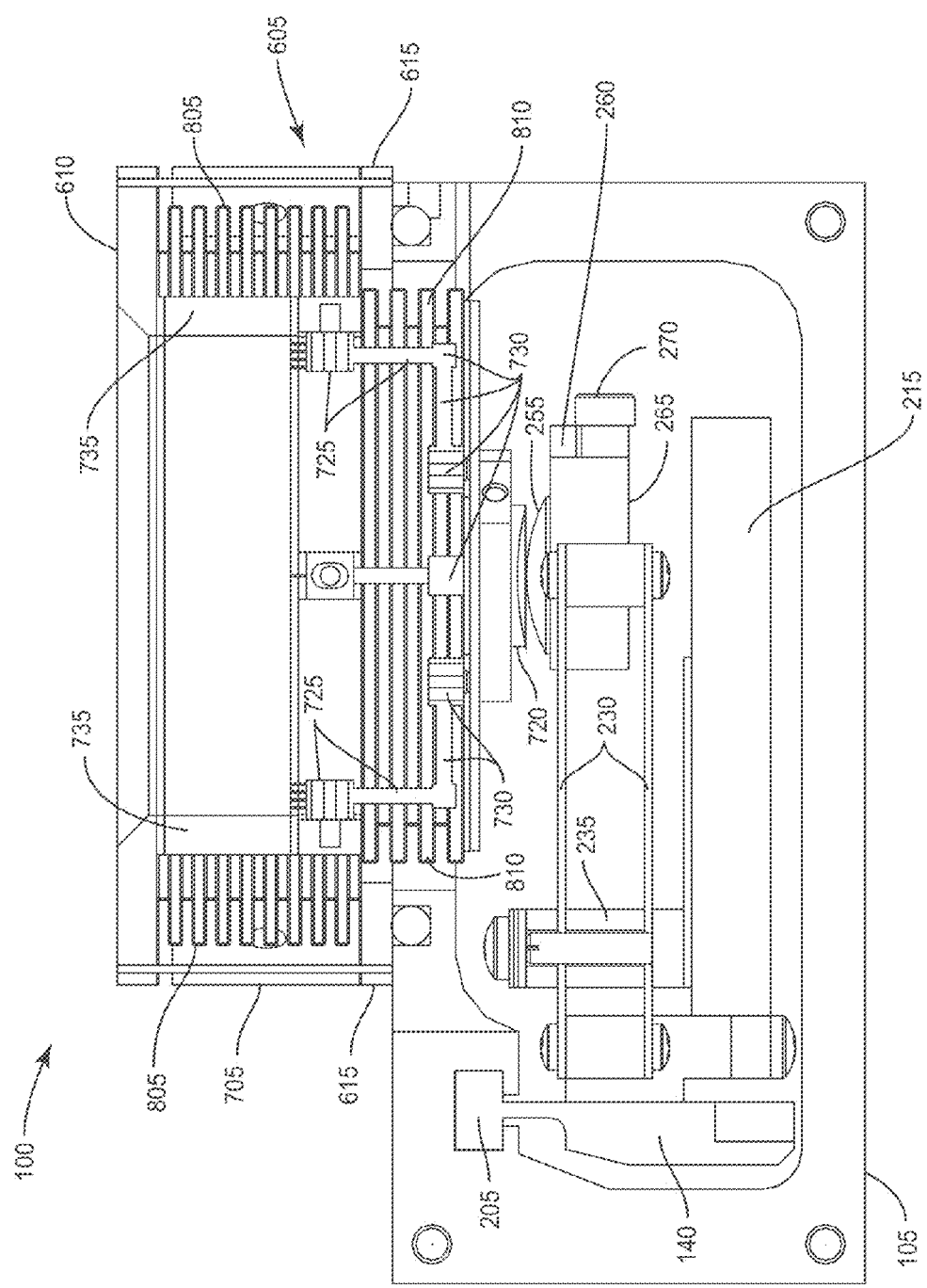
FIG. 9 is a cross-sectional view of a mounting system.

FIG. 9 is a cross-sectional view of the mounting system 100 of FIGS. 6 and 7 according to various embodiments illustrating the lower sample disk 255 and the upper sample disk 720 in close proximity to one another. Depending upon the measurement being taken, the lower sample disk 255 and the upper sample disk 720 may be in contact, or they may be separated by a very small distance. As described previously, first and second micrometers M1, M2 may be used to apply force to the pivot arm 140 causing the pivot arm 140 to bend at the flexing section 415, thereby changing the distance between (or pressure exerted against one another if touching) the lower sample disk 255 and the upper sample disk 720.

As shown in FIG. 9, only the flange 205 of the lower sample mount assembly 135 is in contact with the housing 105 according to various embodiments. All other components of the lower sample mount assembly 135 may be suspended within the hollow space of the housing 105 from the pivot arm 140. This positioning of the lower sample mount assembly 135 allows the lower sample mount assembly 135 to move when the pivot arm 140 flexes in response to a force applied to the pivot arm 140.

Figure 11:
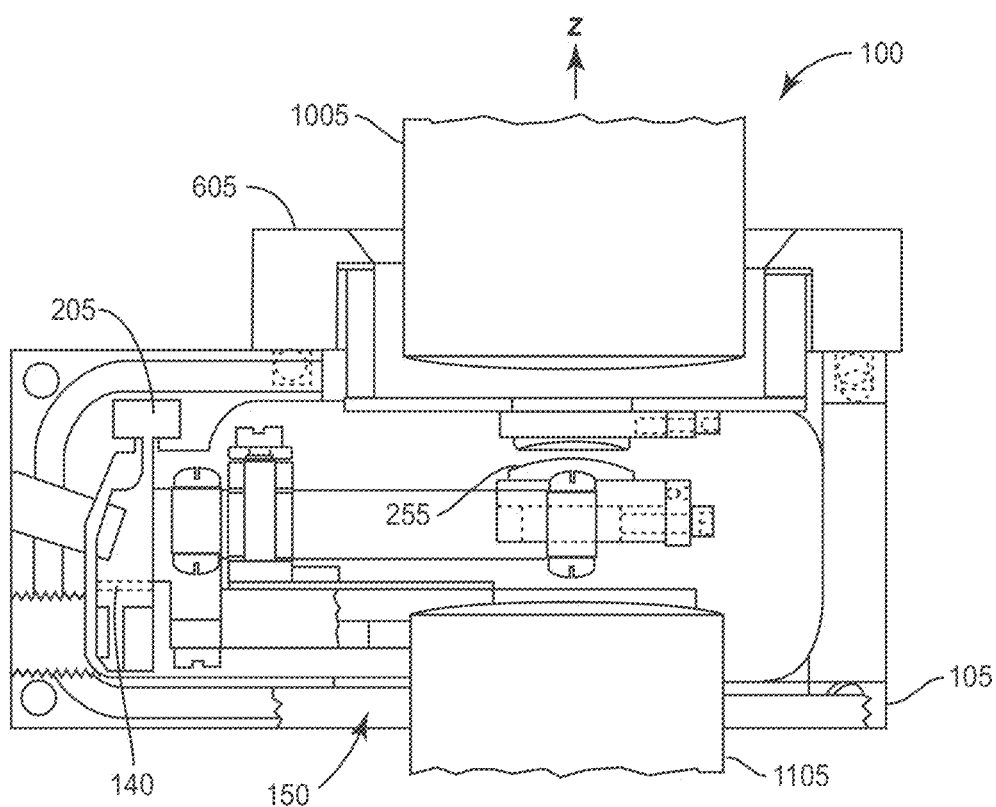
FIG. 11 is a cross-sectional view of a mounting system.

Measurements taken utilizing the mounting system 100 may require direct or indirect visualization techniques, such as optical microscopy, fluorescence microscopy, fluorescence recovery after photobleaching, confocal microscopy, x-ray scattering, reflective or grazing incidence, and the like. FIG. 10 illustrates various embodiments in which visualization instrument 1005 (in this case, an optical microscope objective) may be inserted through the upper mount assembly 605 to gain access to the housing 105 and bring the visualization instrument 1005 in close proximity to the surfaces on the upper sample disk 720 and lower sample disk 255 being visualized. Similarly, FIG. 11 illustrates various embodiments where a visualization instrument 1005 having a wide-diameter objective, which may be advantageous in certain imaging techniques, may be used. FIG. 11 also illustrates various embodiments where a second visualization instrument 1105 may be positioned through the housing bottom surface opening 150 allowing for imaging measurements to be carried out using "inverted microscope" objectives.

Figure 12:
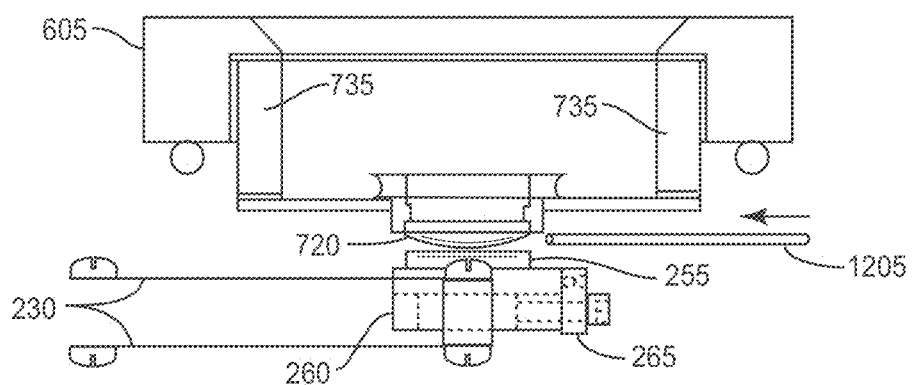
FIG. 12 is a partial side view of a lower sample mount assembly and an upper sample mount assembly.
Figure 13:
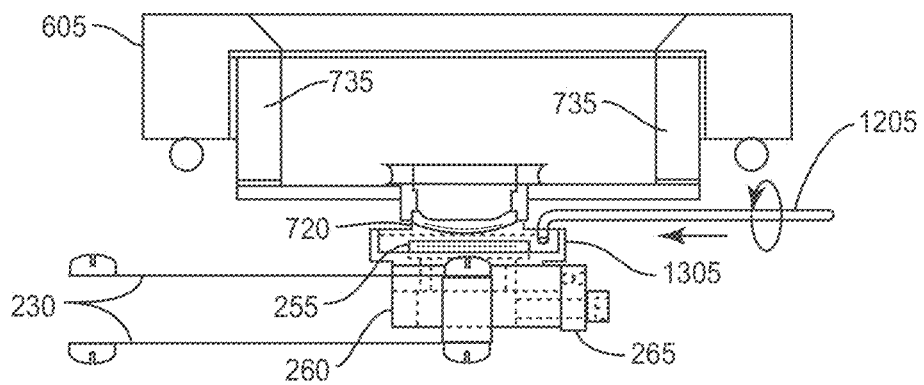
FIG. 13 is a partial side view of a lower sample mount assembly and an upper sample mount assembly.
Figure 14:
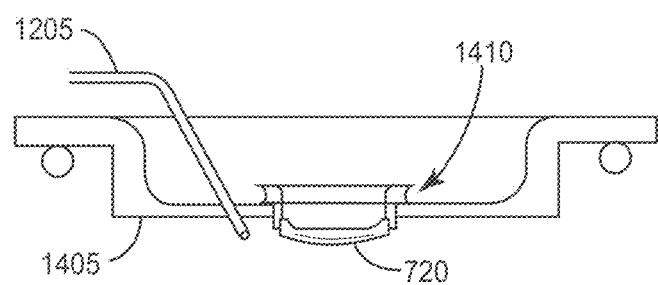
FIG. 14 is a cross-sectional view of an upper sample disk mount holder.

As discussed above, the mounting system 100 may accept many different sample mounts and attachments to perform a wide variety of experiments and measurements. In addition to the sample mounts shown in the previous figures, FIGS. 12 through 14 illustrate various embodiments of sample mounts and attachments according to the present disclosure. It will be obvious to one skilled in the art that the embodiments of FIGS. 12 through 14 are exemplary and should not be considered as limiting the disclosure in any way. FIG. 12 illustrates various embodiments in which the lower sample disk 255 and the upper sample disk 720 have different shapes, as well as the use of a syringe (or other tubing) 1205 to introduce gases, liquids, or other substances onto or about the lower sample disk 255 and the upper sample disk 720. FIG. 13 additionally illustrates the lower sample disk 255 contained within a reservoir 1305 in order to immerse the lower sample disk 255 in a liquid (or other substance) without the need to fill the whole housing 105 with the liquid, according to various embodiments. FIG. 14 illustrates typical embodiments of a rigid upper sample disk mount holder 1405 without the piezoelectric tube 735. The upper sample disk mount holder 1405 may include an opening 1410 to accept interchangeable ("clip-on") upper sample disks 720. Various embodiments may also include a syringe 1205 to introduce gases liquids or other substances as described previously. In various embodiments, both the upper sample disk 720 and the lower sample disk 255 may have a semi-reflecting silver or other suitable light reflecting layer already embedded in the sample disk 255, 720, allowing for immediate optical imaging with FECO or other interference fringe microscopy.

Figure 15A:
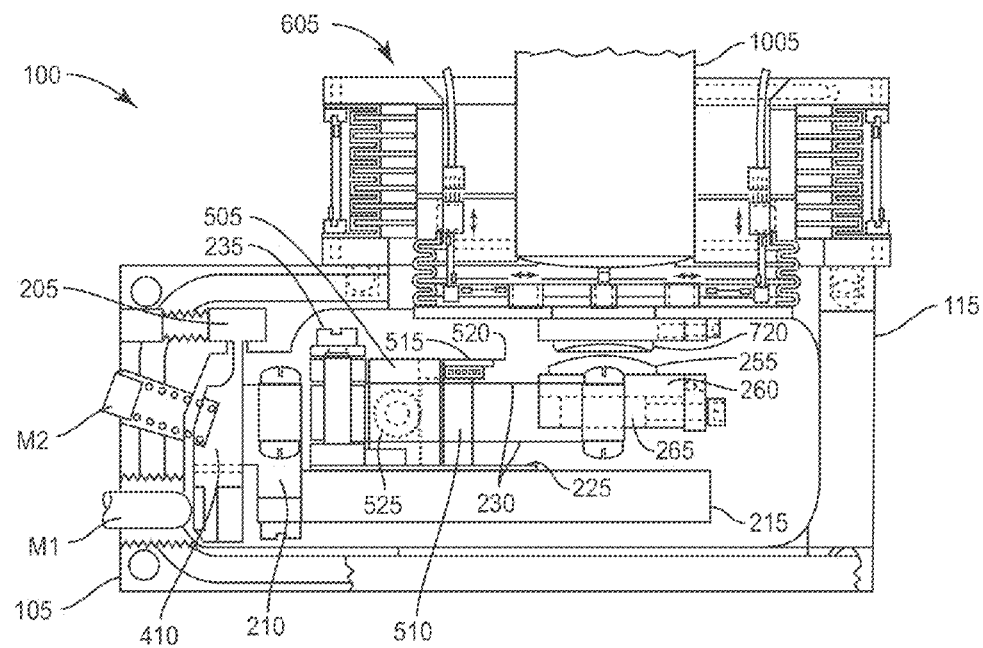
FIG. 15A is a cross-sectional view of a mounting system.
Figure 15B:
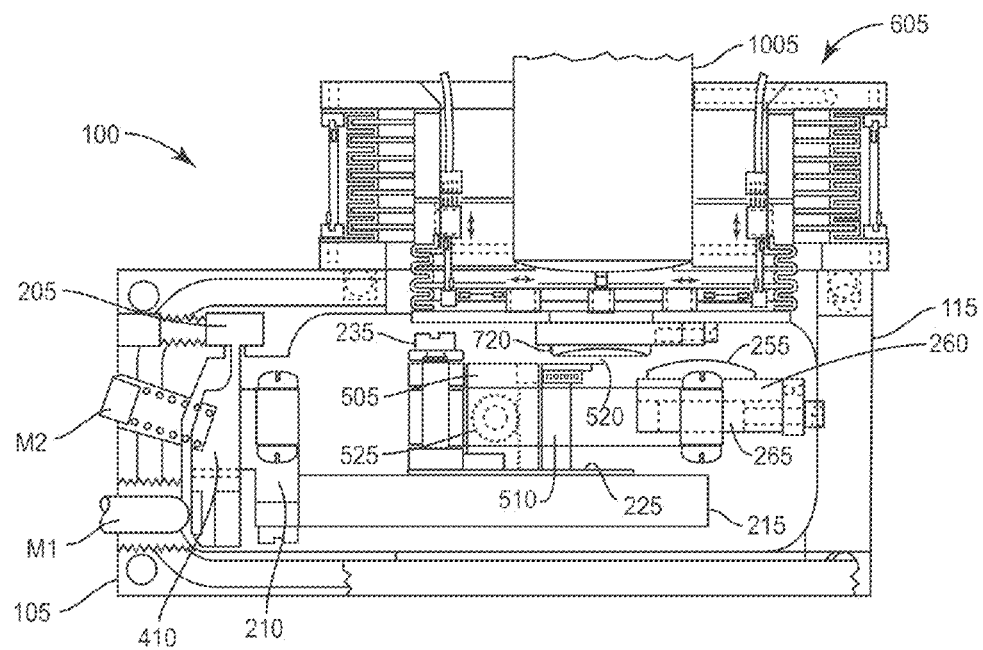
FIG. 15B is a cross-sectional view of a mounting system.

FIGS. 15A and 15B further illustrate the operation of the combined probe tip mounting support 505 and lower sample disk 255 introduced in FIG. 5, shown here in various embodiments with the bellows upper mount assembly 605 (see also the 3-dimensional actuator/sensor upper sample mount 705 in FIG. 7) in place on the housing upper surface 110. In FIG. 15A, the slider 225 is positioned in the guide rails 215 in proximity to the coupling block 210. In this position, the lower sample disk 255 is oriented under upper sample disk 720, allowing experiments and measurements to be conducted based on the interaction of two macroscopic samples or surfaces on the lower sample disk 255 and the upper sample disk 720. In this SFA mode of operation, the probe tip 520 is located apart from the upper sample disk 720 and may not take part in any experiments or measurements.

In FIG. 15B, the slider 225 is moved away from the coupling block 210 and towards the housing front surface 115. Because the probe tip assembly 515 and the lower sample disk mount 260 (via double cantilever springs 230) are coupled to the slider 225, movement of the slider 225 towards the housing front surface 115 moves the lower sample disk 255 away from the upper sample disk 720 and positions the probe tip 520 under the upper sample disk 720. Coarse adjustment of the probe tip 520 height can then be made by turning the probe tip height adjustment knob 525, and fine adjustment may be accomplished with the first and second micrometers M1, M2 and the piezoelectric tube 735 as described previously.

Various embodiments may comprise a sensory-tribological attachment 1605 as the lower sample mount assembly as illustrated in FIGS. 16 through 20. The sensory-tribological attachment 1605 that may be used, for example, to measure sensory properties, as well as thin-film rheology/lubrication, of biological or non-biological surfaces and fluids in thin films (confined geometries). The sensory-tribological attachment 1605 may also be used to quantify transient dynamic tribological behaviors such as stick-slip, stiction spikes, and resonant oscillations (vibrations). Fluorescence imaging may also be used with the sensory-tribological attachment 1605, and certain measurements may be taken with a microscope without the need for FECO optics which may require a spectrometer and complex optics for sub-nanometer resolution imaging.

According to various embodiments, the sensory-tribological attachment 1605 may comprise horizontal double cantilever springs 1609 in the x-y plane and vertical double cantilever springs 1610 in the x-z plane oriented perpendicular to the horizontal double cantilever springs 1609. Each of the horizontal double cantilever springs 1609 and the vertical double cantilever springs 1610 may have strain gauges incorporated into the structure of the springs 1609, 1610. The strain gauges may, for example, be piezo-resistive, semi-conducting, or foil strain gauges. The sensory-tribological attachment 1605 may comprise a motor 1625 held in place by motor mount 1630. The motor mount 1630 may be coupled to each of the vertical double cantilever springs 1610. As described previously, the horizontal double cantilever springs 1609 may be coupled to the coupling block 210, which in turn is coupled to the pivot arm 140. Thus, the sensory-tribological attachment may be displaced in the z-direction (i.e., vertically).

A plurality of wire springs 1620 may be rotatably coupled to the motor 1625, and each wire spring 1620 may terminate with a leveling screw 1615. The leveling screws 1615 may be separately height adjustable in the z-direction. As illustrated in the side view of the sensory-tribological attachment 1605 in FIG. 17, a dish (or disk) 1705 may be coupled to the leveling screws 1615 such that operation of the motor 1625 causes the dish 1705 to rotate. The height-adjustable leveling screws 1615 may allow for the dish 1705 to be made to rotate in essence within the x-y plane, that is, with substantially no wobble which may interfere with accurate tribological measurements. Although not shown in FIG. 17, strain gauges may be coupled to the wire springs 1620 similar to the strain gauges 725, 730, 815 in FIGS. 7 and 8.

Figure 18:
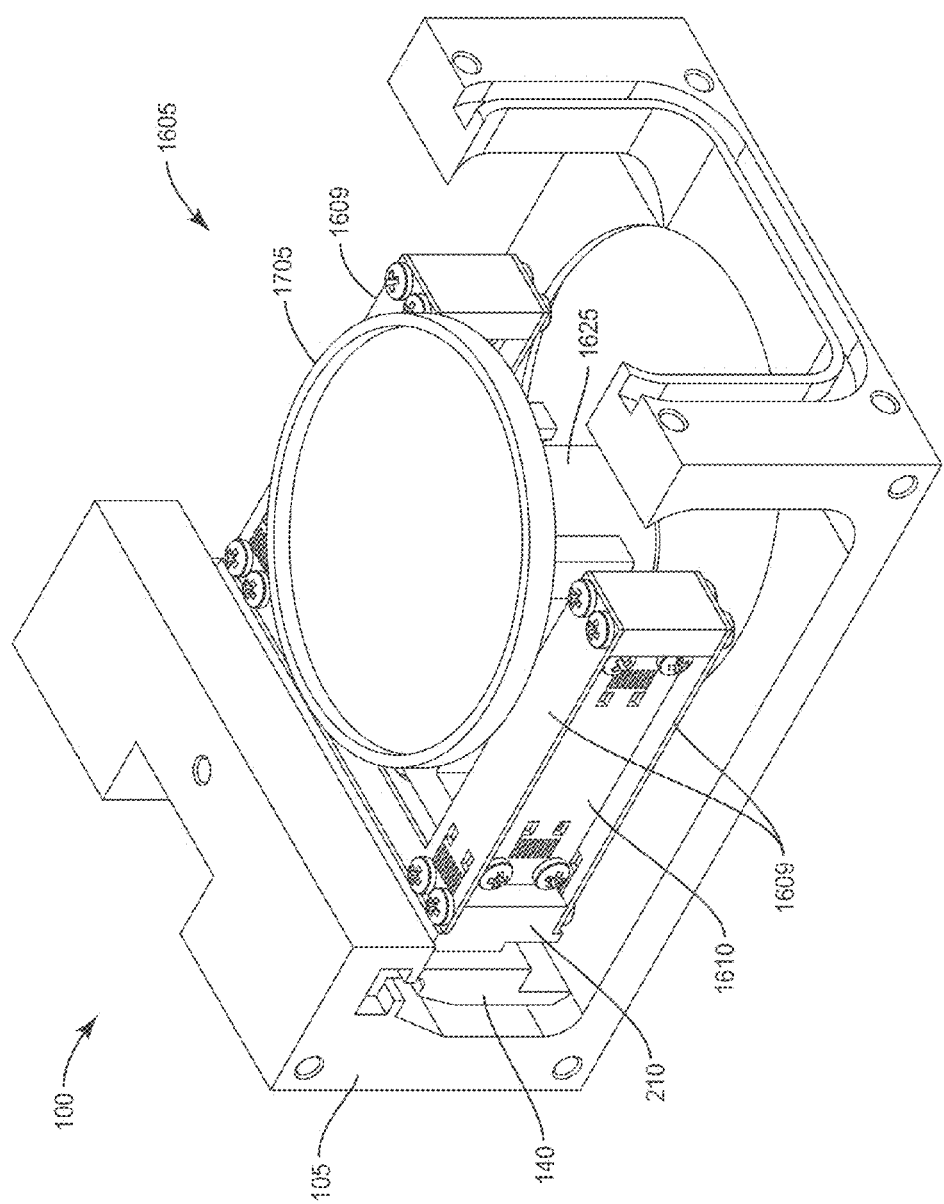
FIG. 18 is a cut-away perspective view of a housing and sensory-tribological attachment.
Figure 19:
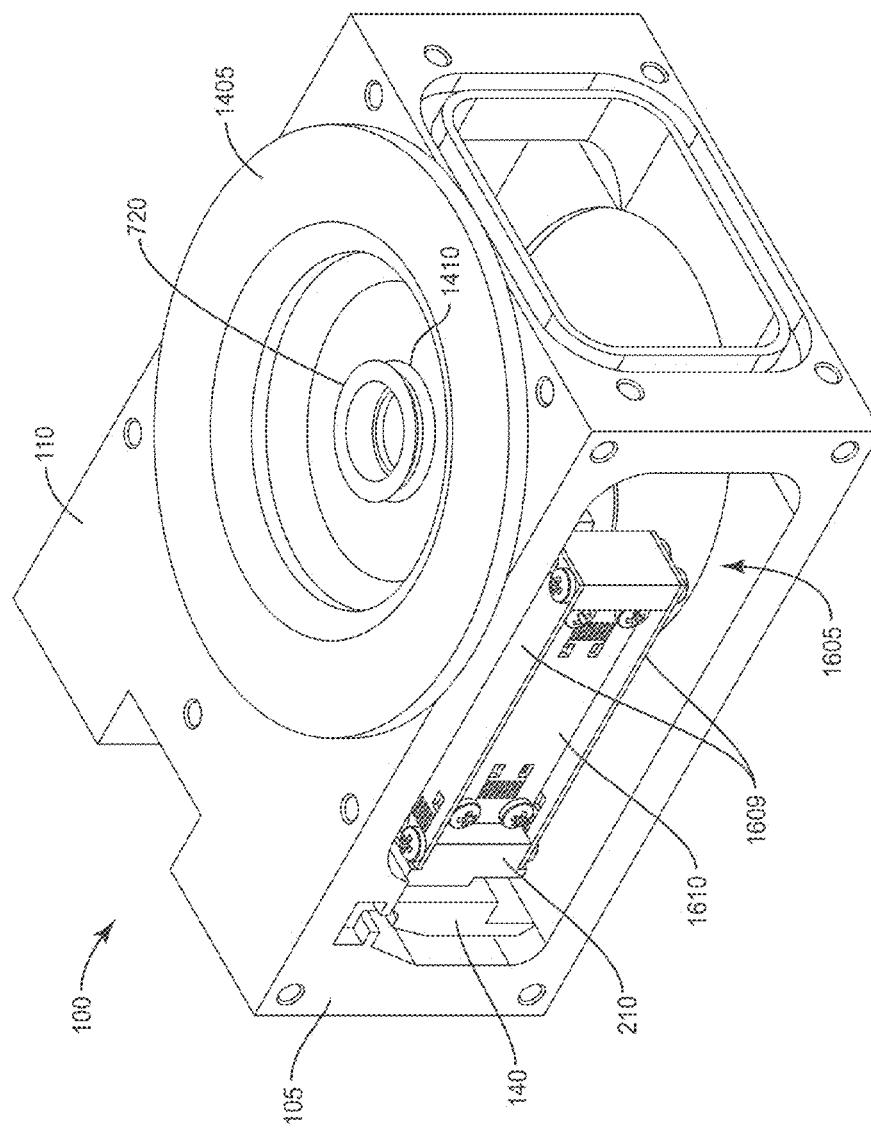
FIG. 19 is a perspective view of a sensory-tribological mounting system.

FIG. 18 illustrates a cut-away perspective view of the housing 105 with the sensory-tribological attachment 1605 mounted in the housing 105 with the dish 1705 in place according to various embodiments. In FIG. 19 according to various embodiments, the upper sample disk mount holder 1405 is positioned on the housing 105, and upper sample disk 720 is positioned in the opening 1410 in the upper sample disk mount holder 1405. The upper sample disk 720 may then contact the dish 1705 or a material or fluid contained in the dish 1705 or deposited on the upper sample disk 720. The normal force between the upper sample disk 720 and the dish 1705 may be measured from the vertical deflection of the horizontal double cantilever springs 1609, as well as a deflection of the wire springs 1620 via the strain gauges (or other measurement device). The lateral (friction) force between the dish 1705 and the upper sample disk 720 may be measured from the horizontal deflection of the vertical cantilever springs 1610, as well as the deflection of the wire springs 1620.

Figure 16:
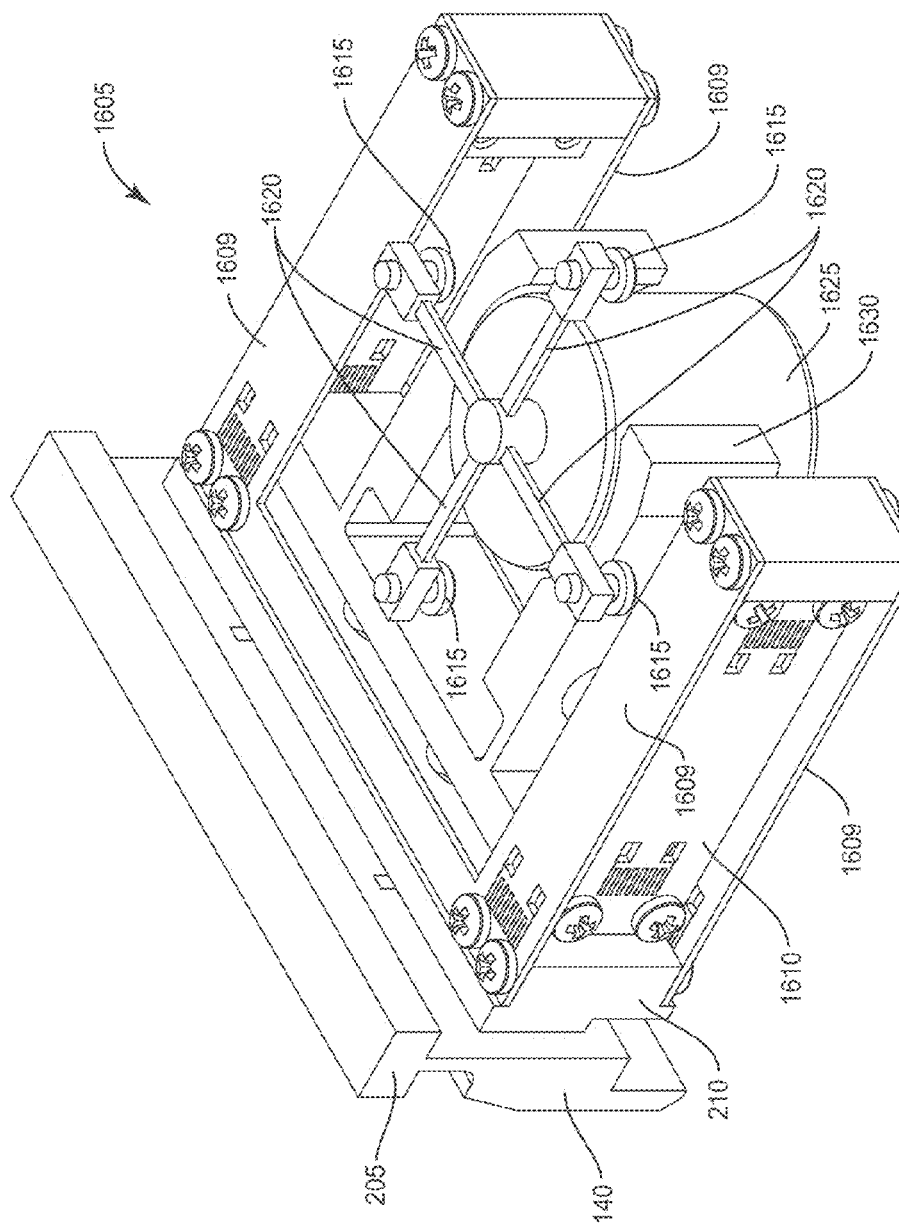
FIG. 16 is a perspective view of a sensory-tribological attachment.
Figure 17:
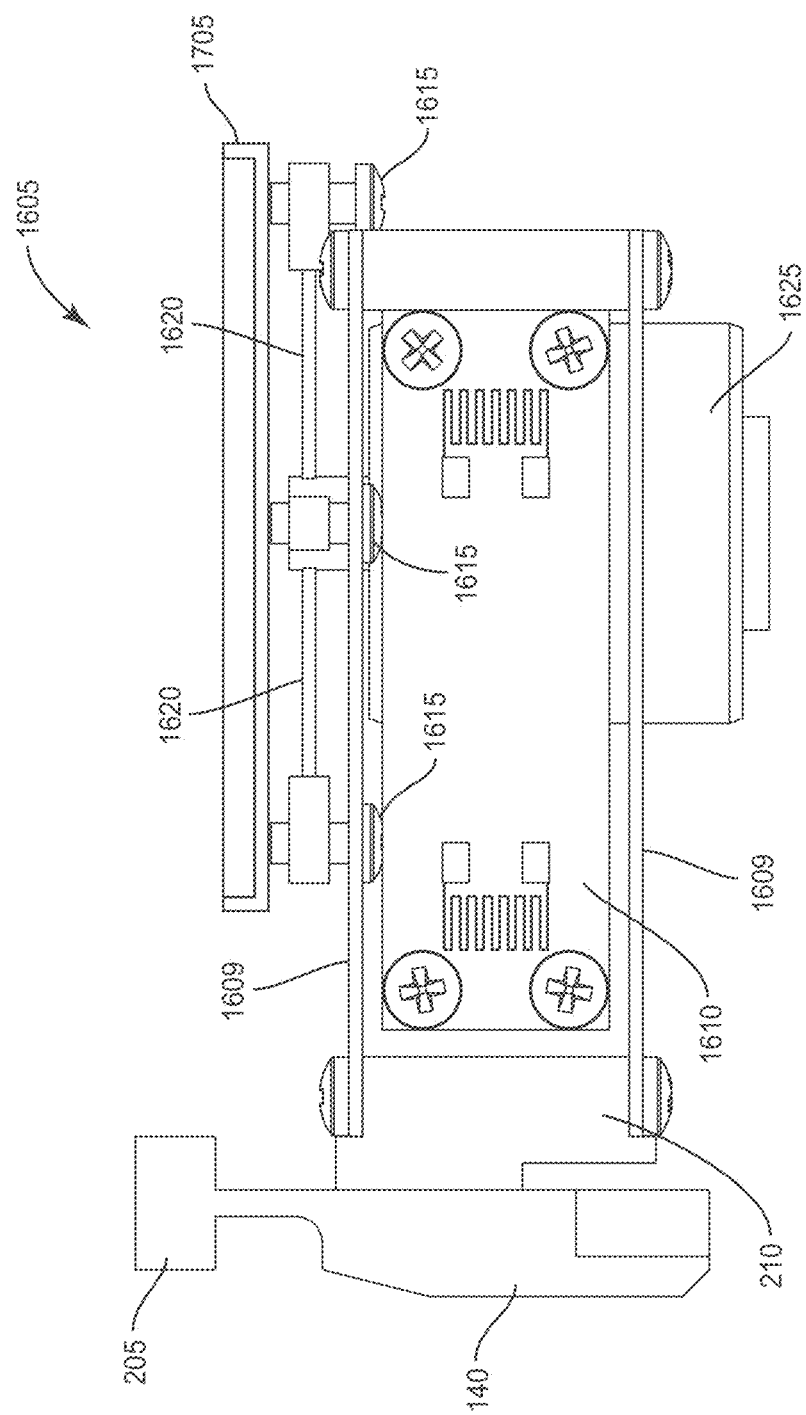
FIG. 17 is a side view of a sensory-tribological attachment.
Figure 20:
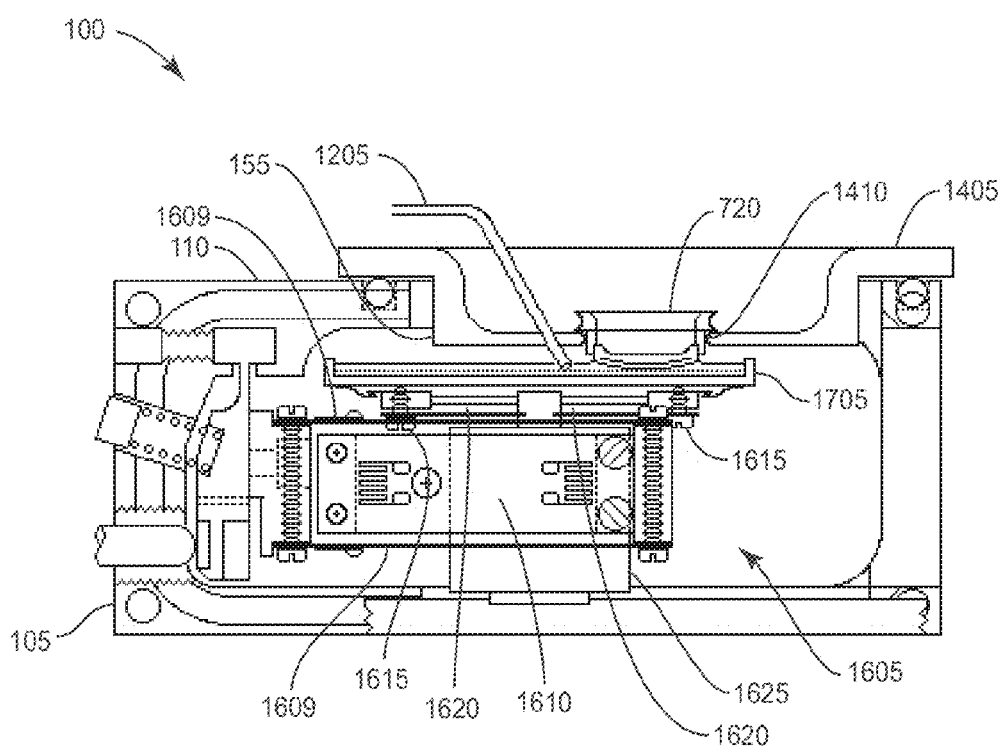
FIG. 20 is a side cross-sectional view of a sensory-tribological mounting system.

FIG. 20 is a cut away side view of the mounting system 100 of FIG. 19 (and the partial views of FIGS. 16, 17, and 18)

according to various embodiments and illustrates upper sample disk 720 in contact with the liquid or other material in the dish 1705.

Figure 21:
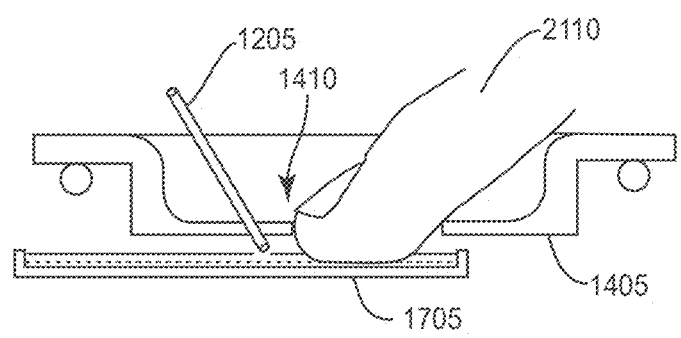
FIG. 21 is a side cross-sectional view of an upper sample disk mount holder.

FIG. 21 illustrates various embodiments of the mounting system 100 of FIG. 20 in which the upper sample "clip on" disk 720 is removed from the upper sample disk mount holder 1405, allowing insertion of a biological sample 2110 (or other sample) through the opening 1410 to make contact with the dish 1705. In various embodiments, the dish 1705 may be an essentially flat disk rather than a dish. The syringe 1205 may be used to introduce gas, liquids, or other substances to the measurement area.

Figure 22:
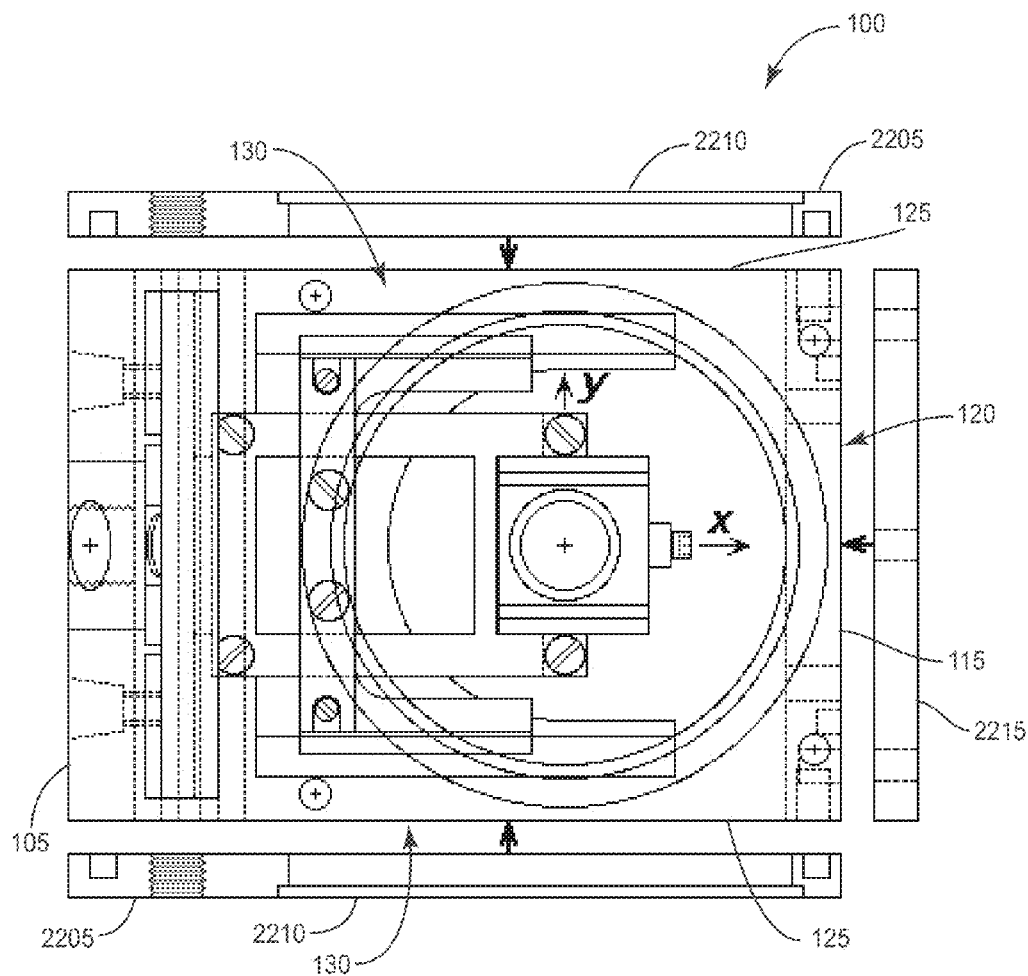
FIG. 22 is a top view of a mounting system with side plates.

For certain experiments and measurements conducted using the mounting system 100, it may be desirable to seal the housing 105 so that the hollow space within the housing 105 may be filled with a liquid or gas or to isolate the hollow space within the housing 105 from any contaminating atmosphere. Sealing the housing 105 is accomplished by covering the side surface openings 130 and front surface opening 120. FIG. 22 illustrates various embodiments of the housing 105 and side plates 2205 and front plate 2215. The front and side plates 2205, 2215 may be coupled to the corresponding side surfaces 125, 126 of the housing 105 by screws, bolts, adhesives, or other techniques as known in the art. The plates may include O-rings or gaskets (not shown) to further facilitate a water-tight or air-tight seal with the housing 105. Windows 2210 may be mounted in the side plates 2205 to allow transmission of light and other electromagnetic waves into the housing 105. For example, the windows 2210 may allow for light or x-rays to be directed both normally (in transmission or reflection) as well as laterally (incidence light) at various angles, which allows multiple optical, x-ray, and spectroscopic (fluorescence, confocal, infrared, and the like) techniques to be used simultaneously. Although not shown in FIG. 22, the front plate 2215 may also include a window 2210. The housing 105 may comprise other opening or ports to allow for insertion of, for example, heating and cooling coils, temperature sensors, syringe injectors, electrical connections, liquid and gas inlets/outlets, and the like. Each of these openings may also be sealed to facilitate a water-tight or air-tight seal.

Figure 23:
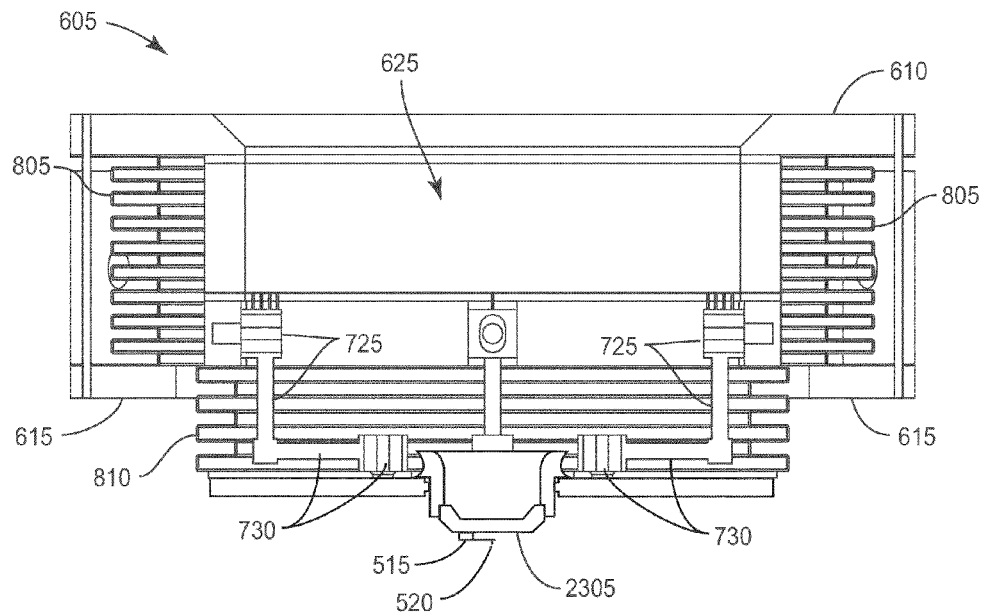
FIG. 23 is a side cross-sectional view of a bellows upper mount assembly.
Figure 24:
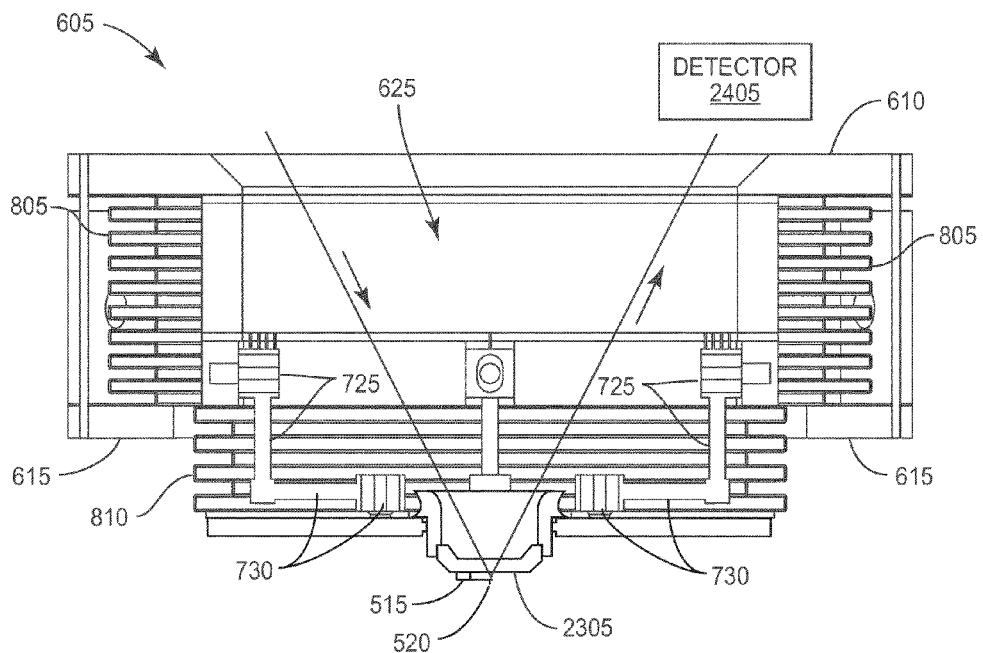
FIG. 24 is a side cross-sectional view of a bellows upper mount assembly.

As illustrated in FIG. 23, various embodiments of the bellows upper mount assembly 605 may allow switching between SFA and AFM modes. In FIG. 24, the upper sample "clip on" disk 720 (which may be used in SFA mode) may be replaced by a probe tip mount 2305. The probe tip mount 2305 may comprise a probe tip assembly 515 and probe tip 520 similar to that illustrated in FIG. 5, except in an inverted orientation. In various embodiments, the probe tip 520 may be, for example, a 3-dimensional piezo-resistive or semi-conducting sensor that points downward (as oriented in FIG. 23). This orientation of the probe tip 520 may allow for AFM-type measurements to be made in an inverted configuration to that shown in FIGS. 5, 15A, and 15B. In various embodiments, this inverted configuration may allow simultaneous force measurements, scanning, and optical, interference and FECO imaging to be conducted with the probe tip 520 and lower sample disk 255 immersed in liquid contained by the reservoir 1305.

FIG. 24 illustrates various embodiments where the bellows upper mount assembly 605 and probe tip mount 2305 may be used with a laser "beam bouncing" method to detect movement of the probe tip 520. A laser beam (or other form of electromagnetic radiation) may be directed into the hollow cylindrical center section 625, through the probe tip mount 2305, and reflecting off the probe tip assembly 515 and back out of the bellows upper mount assembly 605. A detector 2405 may be positioned to receive the reflected laser beam. The detector 2405 may be configured to detect a change in frequency or position of the incoming laser beam and determine the position of the probe tip 520. The various embodiments shown in FIG. 24 allows the placement of sensitive electrical or resistive devices to be located in the hollow cylindrical center section 625 or outside the bellows upper mount assembly 605 and away from corrosive substances that may be in contact with the probe tip 520.

The various configurations of the mounting system 100 described above and illustrated in FIGS. 1 through 24 are intended to be exemplary and are not to be considered the only configurations possible. As will be apparent to one skilled in the art, a wide variety of experiments and measurements may be carried out using the mounting system necessitating the use (or future development) of different sample mounting systems, probes, sensors, and other attachments, all of which are within the scope of the present disclosure.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like are also used to describe various elements, regions, sections, etc., for convenience and are also not intended to be limiting. Like terms refer to like elements throughout the description.

As used herein, the terms "having", "containing", "including", "comprising", and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A mounting system for a surface forces apparatus, the mounting system comprising:
   a housing comprising a plurality of sides defining a hollow space therein;
   a pivot arm comprising a first edge, a body portion and a flexing section extending between the first edge and the body portion;
   a sample mount assembly mounted within the hollow space by the pivot arm, the sample mount assembly comprising a first sample holder;
   a second sample holder positioned in proximity to the first sample holder; and
   at least one load-applying device in contact with the pivot arm;
   the pivot arm being connected at the first edge to the housing to mount the sample mount assembly to the housing;
   whereby operation of the load-applying device causes the pivot arm to bend at the flexing section and thereby move the body portion of the pivot arm relative to the first edge, thereby allowing adjustment of a distance between the first sample holder and the second sample holder.

2. The mounting system of claim 1, wherein the pivot arm comprises a flange along the first edge and a surface of the housing comprises an elongate slot in which the flange is received to mount the sample mount assembly to the housing.

3. The mounting system of claim 1, comprising a spring coupling the sample mount assembly to the body portion of the pivot arm.

4. The mounting system of claim 3, wherein the spring comprises at least two spaced apart cantilever springs.

5. The mounting system of claim 3, wherein the spring is a variable stiffness spring.

6. The mounting system of claim 1, wherein at least one of the plurality of sides of the housing has an opening to provide access to the hollow space, the opening and the sample mount assembly being sized such that the sample mount assembly can be passed into and out of the housing through the opening.

7. The mounting system of claim 1, wherein a first sample mounting surface is removable from the first sample holder without decoupling the first sample holder from the spring.

8. The mounting system of claim 1, wherein a second sample mounting surface is removable from the second sample holder without decoupling the second sample holder from the mounting system.

9. The mounting system of claim 1, wherein the system measures at least seven orders of magnitude of physical properties.

10. The mounting system of claim 1, wherein the system is configured to be received on a microscope stage.

11. The mounting system of claim 1, wherein the system simultaneously takes any combination of any of the following: surface force apparatus measurements; atomic force microscope measurements; and scanning probe microscope measurements.

12. The mounting system of claim 11, wherein the system carries out simultaneous imaging.

13. The mounting system of claim 12, wherein the system is configured to be used with an inverted microscope objective lens.

14. The mounting system of claim 13, wherein the system takes one-, two-, and three-dimensional force measurements.

15. The mounting system of claim 12, wherein the system takes one-, two-, and three-dimensional force measurements.

16. The mounting system of claim 1, wherein the housing is sealed to isolate the hollow space and any components arranged therein from atmospheric contaminants.

17. The mounting system of claim 16, wherein at least one window may be provided in the housing to allow transmission of light and other electromagnetic waves into the sealed housing.

18. The mounting system of claim 16, wherein the housing further comprises sealed ports for permitting insertion of other components into the housing.

19. The mounting system of claim 1, wherein at least one of the sample holders comprises a prefabricated surface.

20. The mounting system of claim 19, wherein the prefabricated surface is removable.

21. The mounting system of claim 1, wherein the pivot arm supports a variety of types of sample mounting assembly.

22. The mounting system of claim 1, wherein the mounting system carries out sensory-tribological measurements in combination with imaging.

23. The mounting system of claim 1, wherein the load-applying device comprises a first micrometer and a second micrometer, the first micrometer being configured to provide coarse distance control and the second micrometer being configured to provide fine distance control.

24. The mounting system of claim 23, wherein the first micrometer is a differential micrometer.

25. The mounting system of claim 24, wherein the pivot arm has a first side at which it is connected to the sample mount assembly and a second side opposite the first side, the first and second micrometer being located on the second side of the pivot arm.

26. The mounting system of claim 23, wherein the pivot arm has a first side at which it is connected to the sample mount assembly and a second side opposite the first side, the first and second micrometer being located on the second side of the pivot arm.

27. The mounting system of claim 1, further comprising a stiffness-adjustable backlash spring that is adapted to act against the pivot arm to minimize backlash and hysteresis.

28. The mounting system of claim 1, wherein at least one of the first sample holder or second sample holder comprises a sealed chamber for preventing exposure of electronic devices in the chamber to corrosive substances.

29. The mounting system of claim 28, wherein the housing further comprises sealed ports for permitting insertion of other components into the housing.

30. The mounting system of claim 1, wherein at least one of the first sample holder or second sample holder comprises a reservoir in which a sample can be immersed.

* * * * *